(12) United States Patent
Miyazaki et al.

(10) Patent No.: US 12,057,198 B2
(45) Date of Patent: Aug. 6, 2024

(54) TERMINAL DEVICE, DATA PROCESSING METHOD, AND PROGRAM

(71) Applicants: Kabushiki Kaisha Toshiba, Minato-ku (JP); Toshiba Digital Solutions Corporation, Kawasaki (JP)

(72) Inventors: Shingo Miyazaki, Tokyo (JP); Masanobu Koike, Tokyo (JP); Fumihiko Sano, Kawasaki Kanagawa (JP); Tatsuro Ikeda, Tokyo (JP); Yoshikazu Hanatani, Tokyo (JP); Taihei Yamaguchi, Chigasaki Kanagawa (JP)

(73) Assignees: KABUSHIKI KAISHA TOSHIBA, Tokyo (JP); TOSHIBA DIGITAL SOLUTIONS CORPORATION, Kawasaki (JP)

( * ) Notice: Subject to any disclaimer, the term of this patent is extended or adjusted under 35 U.S.C. 154(b) by 249 days.

(21) Appl. No.: 17/426,987

(22) PCT Filed: Jan. 30, 2020

(86) PCT No.: PCT/JP2020/003327
§ 371 (c)(1),
(2) Date: Jul. 29, 2021

(87) PCT Pub. No.: WO2020/158842
PCT Pub. Date: Aug. 6, 2020

(65) Prior Publication Data
US 2022/0115093 A1     Apr. 14, 2022

(30) Foreign Application Priority Data
Feb. 1, 2019 (JP) ................. 2019-017395

(51) Int. Cl.
*H04L 29/06* (2006.01)
*G16B 50/40* (2019.01)
(Continued)

(52) U.S. Cl.
CPC ............ *G16B 50/40* (2019.02); *H04L 9/0643* (2013.01); *H04L 67/12* (2013.01)

(58) Field of Classification Search
None
See application file for complete search history.

(56) References Cited

U.S. PATENT DOCUMENTS

| | | | | |
|---|---|---|---|---|
| 6,312,911 B1 * | 11/2001 | Bancroft | ................ | G06N 3/123 435/6.11 |
| 8,904,181 B1 * | 12/2014 | Felsher | ................ | H04L 9/0841 380/282 |
| 9,736,151 B2 * | 8/2017 | Ikeda | ................ | H04L 63/126 |

(Continued)

FOREIGN PATENT DOCUMENTS

| | | |
|---|---|---|
| CN | 1717665 A | 1/2006 |
| EP | 1669877 A1 | 6/2006 |

(Continued)

OTHER PUBLICATIONS

International Search Report issued on Mar. 24, 2020 in PCT/JP2020/003327 filed on Jan. 30, 2020, 2 pages.

(Continued)

*Primary Examiner* — Maung T Lwin
(74) *Attorney, Agent, or Firm* — Maier & Maier, PLLC

(57) ABSTRACT

A terminal device according to an embodiment includes an accepting unit, a secret value generating unit, a response data generating unit, and an output unit. The accepting unit accepts an inquiry about genome data of each user. The secret value generating unit generates a secret value by applying a one-way function to the genome data. The response data generating unit generates response data to the (Continued)

| USER ID | USER DATA | | |
|---|---|---|---|
| | EXTRACTION DATA (X) | DATA POSITION | SECRET-FUNCTION VALUE F(X) |
| ○○○ | $x_1$ | ○○○○ | $f(x_1)$ |
| | $x_2$ | ○○○○ | $f(x_2)$ |
| | ... | ... | ... |
| | $x_k$ | ○○○○ | $f(x_k)$ |
| ... | ... | ... | ... |

70 inquiry on the basis of the secret value generated by the secret value generating unit and contents of the inquiry. The output unit outputs the response data generated by the response data generating unit.

9 Claims, 17 Drawing Sheets

(51) Int. Cl.
*H04L 9/06* (2006.01)
*H04L 67/12* (2022.01)

(56) References Cited

U.S. PATENT DOCUMENTS

| 2013/0044876 A1* | 2/2013 | Shaw | H04L 9/3231 |
| | | | 380/255 |
| 2014/0172830 A1 | 6/2014 | Yoshino et al. | |
| 2016/0085916 A1* | 3/2016 | Smith | G16H 50/70 |
| | | | 705/3 |
| 2016/0283407 A1* | 9/2016 | Van Rooyen | G16H 10/60 |
| 2020/0076798 A1* | 3/2020 | Lidsky | H04L 9/3228 |

FOREIGN PATENT DOCUMENTS

| JP | 2013114534 A | 6/2013 |
| JP | 2016-206918 A | 12/2016 |
| WO | WO 2016/083949 A1 | 6/2016 |

OTHER PUBLICATIONS

Office Action issued on May 7, 2024, in corresponding Chinese Application No. 202080011513.6, 8 pages.

* cited by examiner

FIG. 3

| USER ID | USER DATA | | |
|---|---|---|---|
| | EXTRACTION DATA (X) | DATA POSITION | SECRET-FUNCTION VALUE F(X) |
| ○○○ | $x_1$ | ○○○○ | $f(x_1)$ |
| | $x_2$ | ○○○○ | $f(x_2)$ |
| | ... | ... | ... |
| | $x_k$ | ○○○○ | $f(x_k)$ |
| ... | ... | ... | ... |

| INQUIRY CONTENTS | | |
|---|---|---|
| ESTIMATION TARGET | COMPARISON DATA ($Y_{adr}$) | DATA POSITION (adr) |
| ALCOHOL TOLERANCE | ○○○○ | ○○○○ |
| ASTHMA | ○○○○ | ○○○○ |
| DIABETES | ○○○○ | ○○○○ |
| ... | ... | ... |

| USER TYPE | FORM OF INQUIRY | | | NUMBER OF CONSECUTIVE INQUIRY REQUEST | COMMAND RECEPTION RECOVERY TIME |
|---|---|---|---|---|---|
| | SCENE 1 (SINGLE BASE SEQUENCE) | SCENE 2 (GENOME WIDE ASSOCAITION ANALYSIS) | SCENE 3 (POLY GENERIC SCORE) | | |
| MEDICAL WORKER | ○ | ○ | ○ | 10 | 5 MINUTES |
| GENERAL SERVICE | ○ | △ (UP TO THREE TYPE) | × | 1 | 30 MINUTES |

90

TERMINAL DEVICE, DATA PROCESSING METHOD, AND PROGRAM

TECHNICAL FIELD

Embodiments of the present invention relate to a terminal device, a data processing method, and a program.

BACKGROUND ART

Conventionally, user-specific personal information is managed in various fields. For example, in the fields of medicine and pharmaceuticals, in order to estimate genetic characteristics, genome data of patients or subjects is used. Particularly, confidentiality of genome data is treated with the utmost importance and the information is managed with strong information security. However, for example, when contents desired by a user such as genetic characteristics and the like of the user are estimated using genome data of the user as it is, there is concern of the genome data being leaked to the outside, in other words, there is concern of security not being able to be maintained. In a case in which the corresponding genome data is encrypted using a reversible encryption function and is recorded or transmitted and received through communication, in view of imperilment of the encryption function and progress of computation performance of computers or distributed computing, there is concern of the genome data that is permanent personal information being decrypted, and the genome data from the entire life of a corresponding user being exposed.

CITATION LIST

Patent Literature

[Patent Literature 1]
Japanese Unexamined Patent Application, First Publication No. 2018-503167

SUMMARY

A terminal device according to an embodiment includes an accepting unit, a secret value generating unit, a response data generating unit, and an output unit. The accepting unit accepts an inquiry about genome data of each user. The secret value generating unit generates a secret value by applying a one-way function to the genome data. The response data generating unit generates response data to the inquiry on the basis of the secret value generated by the secret value generating unit and contents of the inquiry. The output unit outputs the response data generated by the response data generating unit.

BRIEF DESCRIPTION OF DRAWINGS

FIG. 3 is a diagram illustrating an example of a user data table 70 stored in a secret value storing unit 106.

FIG. 4 is a diagram illustrating an example of an inquiry contents table 80 stored in a client device 20.

FIG. 14 is a diagram illustrating an example of a form of an inquiry for each type of user.

DESCRIPTION OF EMBODIMENTS

Hereinafter, a terminal device, a data processing method, and a program according to embodiments will be described with reference to the drawings.

First Embodiment

Figure 1:
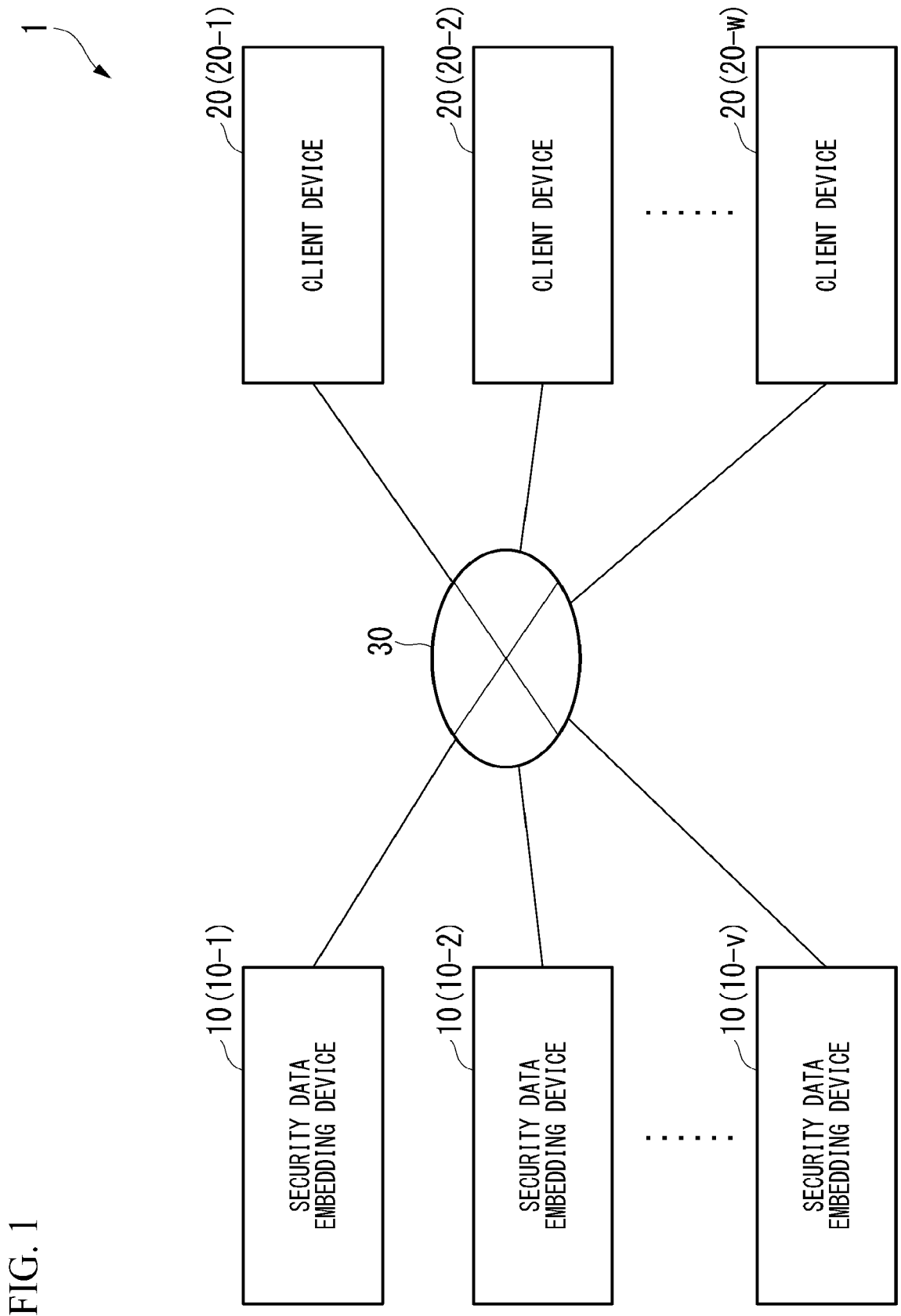
FIG. 1 is a diagram illustrating an example of the entire configuration of a sealing system 1 according to this embodiment.

FIG. 1 is a diagram illustrating an example of the entire configuration of a sealing system 1 according to this embodiment. The sealing system 1 includes security data embedding devices 10 and client devices 20. The security data embedding devices 10 and the client devices 20 communicate with each other via a network 30.

For example, the network 30 includes the Internet, a wide area network (WAN), a local area network (LAN), a cellular network, Wi-Fi (registered trademark), Bluetooth (registered trademark), near field communication (NFC), infrared communication, a body area network, or the like.

For example, the security data embedding devices 10-1 to 10-$v$ are each owned by different users. In addition, the client devices 20-1 to 20-$w$ are each owned by different users. The security data embedding devices 10-1 to 10-$v$ and the client devices 20-1 to 20-$w$ may have a relation of one-to-one correspondence. Users of the security data embedding devices 10-1 to 10-$v$ and users of the client devices 20-1 to 20-$w$ may not coincide with each other. For example, the client devices 20-1 to 20-$w$ may be security data embedding devices connecting terminals of a medical institution that access the security data embedding devices 10-1 to 10-$v$ of medical examinees or patients through contact or non-contact communication.

In the following description, in a case in which the individual security data embedding devices 10-1 to 10-$v$ do not need to be distinguished from each other such as a case in which common matters are described or the like, the security data embedding devices 10-1 to 10-v will be simply referred to as a security data embedding device 10. Similarly, the client devices 20-1 to 20-w will be simply referred to as a client device 20.

The security data embedding device 10 is an example of a terminal device. For example, the security data embedding device 10 may be a computer device of a portable type. The security data embedding device 10 may be a dedicated computer device or may be a computer device having versatility such as a smartphone or a tablet device in which predetermined application software (hereinafter referred to as an "application") can be installed. The security data embedding device 10 is in the form of a user identity module (UIM) and may be formed to be able to be detachably connected to a smartphone or a tablet device. The client device 20 may be a computer device such as a smartphone, a tablet terminal, a personal computer, a notebook computer, a facility-installed terminal, or the like. A predetermined application is installed in the client device 20.

Figure 2:
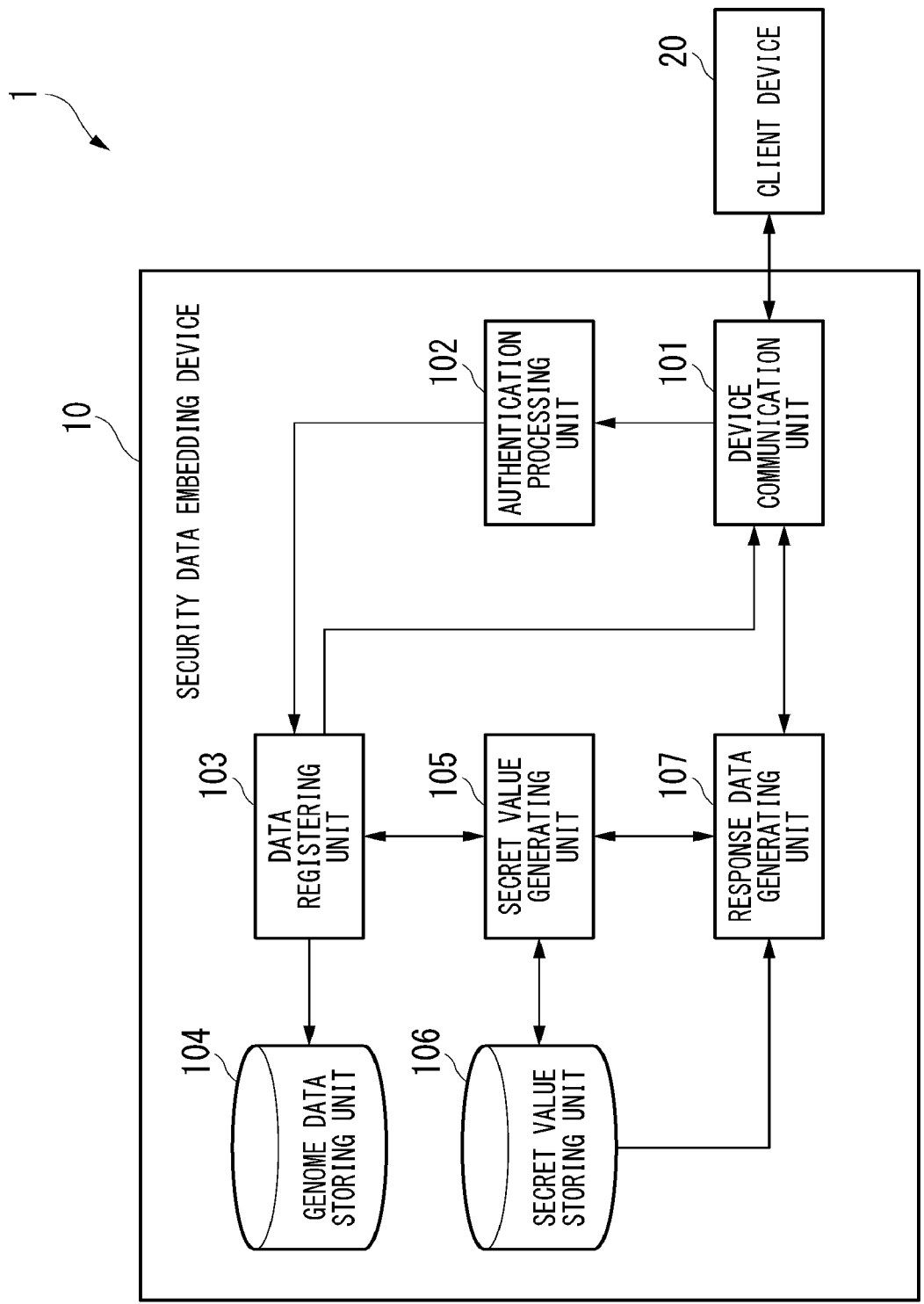
FIG. 2 is a schematic block diagram illustrating the configuration of functional blocks of the sealing system 1 according to this embodiment.

FIG. 2 is a schematic block diagram illustrating the configuration of functional blocks of the sealing system 1 according to this embodiment. The security data embedding device 10 includes a device communication unit 101, an authentication processing unit 102, a data registering unit 103, a genome data storing unit 104, a secret value generating unit 105, a secret value storing unit 106, and a response data generating unit 107.

The device communication unit 101 is a communication interface. The device communication unit 101 communicates with the client devices 20 through the network 30. For example, the device communication unit 101 can perform near field communication with the client devices 20. The device communication unit 101 receives authentication data used for authentication of the client device 20, contents of an inquiry about genome data of a user accepted from the client device 20, and original data of genome data of the user at the time of initial registration.

The genome data includes data relating to a base sequence. For example, an inquiry about genome data of a user is an inquiry about genetic characteristics of the user. More specifically, an inquiry about genome data of a user is an inquiry about a constitution, characteristics, capabilities, risks for diseases (for example, asthma, anxiety, diabetes, cancer, dementia, and the like), and the like of the user. More specifically, an inquiry about genome data of a user is an inquiry about a sequence at a predetermined position of the genome data or an inquiry about specific bases or values of all the bases in the genome data. Although a case in which genome data is stored as original data will be described in this embodiment, the original data is not limited to genome data and may be personal information (user data) in which numbers and symbols are arranged.

In addition, although contents of an inquiry about genome data of a user and authentication data are configured to be accepted in accordance with reception from the device communication unit 101 in this embodiment, the configuration is not limited thereto, and the contents of the inquiry and the authentication data may be accepted in accordance with an input from a user. More specifically, an input screen of contents which can be inquired about or authentication data may be displayed in a display unit, which is not illustrated, included in the security data embedding device 10, and contents of an inquiry about genome data of a user or authentication data may be accepted in accordance with a user's selection. In addition, the device communication unit 101 is an example of an accepting unit and an output unit.

The authentication processing unit 102, the data registering unit 103, the secret value generating unit 105, and the response data generating unit 107 are realized, for example, by a hardware processor such as a central processing unit or the like executing a program (software). Some or all of such constituent elements may be realized by hardware (a circuit unit; including circuitry) such as a large scale integration (LSI), an application specific integrated circuit (ASIC), a field-programmable gate array (FPGA), a graphics processing unit (GPU), or the like or may be realized by software and hardware in cooperation. The program may be stored in a storage device (a storage device including a non-transitory storage medium) such as a hard disk drive (HDD), a flash memory, or the like in advance or may be stored in a storage medium (a non-transitory storage medium) such as a DVD, a CD-ROM, or the like that can be loaded and unloaded and be installed by the storage medium being loaded into a drive device. The program may be stored in a storage that non-temporarily stores programs. By executing a program stored in the storage unit 110 using a processor, the functions of the security data embedding device 10 are realized.

Next, initial registration of original data will be described. When authentication data or genome data is received from the client device 20, the device communication unit 101 outputs the received data to the authentication processing unit 102. The authentication processing unit 102 performs authentication using authentication data output from the device communication unit 101. The authentication data includes data indicating an issuance subject of genome data and an identification (ID) and a password of a user. Here, biometric authentication data used for personal authentication of a corresponding user may be included in the authentication data.

The authentication processing unit 102 performs judgment of validity of an issuance subject using data that indicates an issuance subject of genome data or judgment of validity of an ID and a password of a user. In a case in which results of the two judgments are "valid", the authentication processing unit 102 judges that authentication has been successful.

On the other hand, in a case in which the result of at least one of the two judgments is "not valid", the authentication processing unit 102 judges that authentication has been unsuccessful. In a case in which the authentication has been unsuccessful, the authentication processing unit 102 outputs information representing an indication of unsuccessful authentication to the device communication unit 101. In addition, a reason for the unsuccessful authentication may be included in the information representing an indication of unsuccessful authentication. For example, the reason for unsuccessful authentication is a detail representing which of the two judgments is No. The device communication unit 101 transmits information (error information) representing an indication of unsuccessful authentication, which is output from the authentication processing unit 102, to the client device 20. Then, the client device displays an indication of unsuccessful authentication.

Although authentication using the authentication processing unit 102 is configured to be performed only when original data is initially registered, the configuration is not limited thereto, and the authentication may be performed also when there is an inquiry about genome data that is performed thereafter. At that time, a form in which judgment of personal authentication for checking whether or not someone is an owner of a corresponding security data embedding device is performed using biometric authentication data included in authentication data may be employed.

In a case in which authentication has been successful, the authentication processing unit 102 transmits an ID of a user and original data to the registering unit 103.

In a case in which an ID of a user and original data are not stored in the genome data storing unit 104, the data registering unit 103 causes the storage unit 104 to store an ID of a user and original data output from the authentication processing unit 102. On the other hand, in a case in which an ID of a user and original data are stored in the genome data storing unit 104, the data registering unit 103 does not cause the storage unit 104 to store the ID of the user and the original data. In other words, writing from the data registering unit 103 is set to be valid only in a case in which genome data is not stored in the genome data storing unit 104.

For this reason, the genome data storing unit 104 stores only genome data of one user. However, the genome data storing unit 104 may store genome data of a plurality of users. In such a case, in a case in which genome data of the same person is stored in advance, the writing of the genome data is invalidated, and writing of genome data may be validated for genome data of other users (genome data that has not been registered). In addition, the genome data may be stored in association with an ID of each user. In this embodiment, although the genome data storing unit 104 is disposed in the security data embedding device 10, the configuration is not limited thereto, and, for example, the genome data storing unit 104 may be disposed in an external device such as an external server or the like.

The genome data storing unit 104 is a storage device such as a magnetic hard disk device, a semiconductor storage device, or the like. Original data that is stored in the genome data storing unit 104 once is thereafter prohibited from being output (read) to the outside. For example, the genome data storing unit 104 is configured to be prohibited from outputting original data to the outside in accordance with a structure on hardware. More specifically, only the data registering unit 103 is wired to be connectable to the genome data storing unit 104, and only the data registering unit 103 can write data into the genome data storing unit 104.

In addition, data stored in the genome data storing unit 104 cannot be read from any of the functional units including the data registering unit 103. Furthermore, functional units other than the data registering unit 103 may be also wired to be connectable to the genome data storing unit 104. However, also in such a case, only the data registering unit 103 may have a right to access the genome data storing unit 104, and outputting (reading) of original data stored in the genome data storing unit 104 to the outside may be prohibited.

In addition, when original data is stored in the genome data storing unit 104, the data registering unit 103 outputs an ID and extraction data X that is data of a part (or all) of the original data to the secret value generating unit 105. The extraction data X is data used for estimating genetic characteristics of a user. More specifically, the extraction data X includes information representing a sequence of a predetermined position in genome data and a value (the strength of influence) of specific bases (or all the bases) in the genome data.

The secret value generating unit 105 generates a secret-function value F(X) as a secret value of extraction data X output from the data registering unit 103. In the generation of the secret-function value F(X), an irreversible one-way function is used. The secret value generating unit 105 generates the secret-function value F(X) by applying the same one-way function to the extraction data X formed in a series of data. Different one-way functions may be applied to the plurality of data rows included in the extraction data X.

Here, for example, in preparation for an inquiry about alcohol tolerance, the response data generating unit 107 generates a secret-function value $f(x_p)$ of information $x_p$ representing an array of data positions p that are focused on for judgment of alcohol tolerance. In addition, in preparation for an inquiry about diseases such as asthma and the like, the response data generating unit 107 generates secret-function values $f(x_1), f(x_2), \ldots, f(x_k)$ by applying one-way functions of values of a plurality of (for example, k) bases included in the extraction data X. Here, k may be the number of all the bases in genome data or may be the number of specific bases focused on when genetic characteristics of a user are estimated.

The secret value generating unit 105 stores the generated secret-function value F(X) and an ID output from the data registering unit 103 in the secret value storing unit 106 in association with each other. In addition, in a case in which secret-function values $f_p(x_p)$ are generated by applying different one-way functions $f_p$ to information $x_p$ of data positions p, the secret value generating unit 105 may store each data position and each one-way function $f_p$ applied to each piece of information $x_p$ in the secret value storing unit 106 in association with each other. An example of data stored in the secret value storing unit 106 will be described below with reference to FIG. 3.

In addition, although the secret value generating unit 105 is configured to generate a secret-function value F(X) at the time of initial registration of genome data and store the generated secret-function value in the secret value storing unit 106, the configuration is not limited thereto. For example, the secret value generating unit 105 may generate a secret-function value F(X) every time there is an inquiry without storing the secret-function value F(X) in the secret value storing unit 106. In such a case, the security data embedding device 10 may include a part data storing unit (not illustrated) that stores data that is partial data of original data and is in preparation for an inquiry when the original data is initially registered. Then, the secret value generating unit 105 may generate a secret-function value F(X) of the corresponding part data by referring to the part data storing unit at a timing at which there is an inquiry.

The secret value storing unit 106 is a storage device such as a magnetic hard disk device, a semiconductor storage device, or the like. Differently from the genome data storing unit 104, the secret value storing unit 106 can output read stored information (the secret-function value F(X)) to the outside. In addition, even in a case in which the secret-function value F(X) is stored in the secret value storing unit 106, the secret-function value can be also written by the secret value generating unit 105. Furthermore, the secret value storing unit 106 is not limited to being disposed in the security data embedding device 10 and, for example, may be disposed in an external device such as an external server or the like.

When an ID and a secret-function value F(X) are stored in the secret value storing unit 106, the secret value generating unit 105 outputs information representing an indication of a registration process being successful to the data registering unit 103. The information representing an indication of a registration process being successful is transmitted to the client device 20 through the data registering unit 103 and the device communication unit 101. Then, the client device 20 displays the indication of a registration process being successful.

Next, an inquiry about genome data will be described. When contents of an inquiry are received from the client device 20, the device communication unit 101 outputs the received contents to the response data generating unit 107.

The response data generating unit 107 outputs the contents of the inquiry output from the device communication unit 101 to the secret value generating unit 105. In the contents of the inquiry, comparison data is included. For example, the comparison data includes data to be compared with a sequence at a predetermined position of genome data. In a case in which contents of an inquiry are alcohol tolerance, for example, a sequence at a predetermined position is a sequence at a data position p focused on for judgment of presence/absence of alcohol tolerance. In addition, the comparison data is a data used for a comparison that represents a sequence representing having alcohol tolerance (or a sequence representing having no alcohol tolerance).

The comparison data includes data to be compared with specific bases in genome data. For example, in a case in which contents of an inquiry represent "a risk of asthma," the specific bases are a plurality of bases focused on for judgment of "a risk of asthma." In addition, the comparison data is a value used for a comparison that indicates that there is a risk of asthma (or there is no risk of asthma) for each base.

In addition, the contents of an inquiry include each piece of comparison data to be compared with values of all the bases in genome data. For example, in a case in which contents of an inquiry represent "a risk of anxiety," all the bases are all the bases that are focused on for judgment of "a risk of anxiety." In addition, each piece of comparison data is a value used for a comparison that indicates that there is a risk of anxiety (or there is no risk of anxiety) for each base.

The secret value generating unit 105 generates a secret comparison value F(Y) that is secret by applying a one-way function to the comparison data Y included in the contents of an inquiry. In the generation of the secret comparison value F(Y), the same function as the one-way function used for generation of the secret-function value F(X) is used. In a case in which the comparison data Y includes a plurality of pieces of comparison data y, the secret value generating unit 105 generates secret comparison values $f(y_1)$, $f(y_2)$, ..., $f(y_k)$ by applying a one-way function to each piece of comparison data y. Here, secret-function values $f_p(x_p)$ can be generated also by applying different one-way functions $f_p$ to each piece of information $x_p$ of each data position p, and in such a case, the secret value storing unit 106 stores each data position p and each one-way function $f_p$ applied to the information $x_p$ in association with each other. In addition, in such a case, the secret value generating unit 105 may generate a secret comparison value $f_p(y_p)$ by applying a one-way function stored in association with a data position p to comparison data $y_p$ of the data position p in the comparison data y. When the secret comparison value F(Y) is generated, the secret value generating unit 105 outputs the generated secret comparison value F(Y) to the response data generating unit 107.

The response data generating unit 107 generates response data for an inquiry on the basis of the secret-function value F(X) stored in the secret value storing unit 106 and the secret comparison value F(Y) output from the secret value generating unit 105. For example, the response data is data that indicates whether or not the secret-function value F(X) and the secret comparison value F(Y) coincide with each other. For example, in a case in which alcohol tolerance is judged, the response data is data that indicates whether or not the secret-function value $f(x_p)$ of the information $x_p$ representing the sequence of the data position p focused on for judgment of alcohol and the secret comparison value $f(y_p)$ of the comparison data $y_p$ representing the sequence of the data position p coincide with each other. The response data generating unit 107 generates response data indicating that "there is alcohol tolerance" in a case in which the secret-function value $f(x_p)$ and the secret comparison value $f(y_p)$ coincide with each other and generates response data indicating that "there is no alcohol tolerance" in a case in which the secret-function value $f(x_p)$ and the secret comparison value $f(y_p)$ do not coincide with each other The response data is response data based on a result of comparison between the secret-function value F(X) and the secret comparison value F(Y). It is assumed that contents of an inquiry represent, for example, "a risk of asthma," and the number of specific bases focused on for judgment of "a risk of asthma" is, for example, s. In this case, the response data generating unit 107 generates response data such as the number of coincidences (a degree of coincidence), a ratio of coincidence (a coincidence rate), or the like between secret values $f(x_1)$, $f(x_2)$, ..., $f(x_s)$ and secret comparison values $f(y_1)$, $f(y_2)$, ..., $f(y_s)$.

In addition, for example, it is assumed that contents of an inquiry represent "a risk of anxiety," and the number of all the bases focused on for judgment of "a risk of anxiety" is t. In this case, the response data generating unit 107 generates response data based on a value weighted in accordance with whether or not secret values $f(x_1)$, $f(x_2)$, ..., $f(x_t)$ and secret comparison values $f(y_1)$, $f(y_2)$, ..., $f(y_t)$ respectively coincide with each other. The response data based on a weighted value, for example, is an accumulated value that is acquired by performing weighting in a case in which secret values $f(x_1)$, $f(x_2)$, ..., $f(x_k)$ and secret comparison values $f(y_1)$, $f(y_2)$, ..., $f(y_k)$ respectively coincide with each other. For example, the weighting is addition of a predetermined number or multiplication by a predetermined number.

Although the secret-function value F(X) used for generation of response data by the response data generating unit 107 is the secret-function value F(X) stored in the secret value storing unit 106 in the description presented above, the secret-function value described above is not limited thereto. For example, a secret-function value F(X) generated by an external device can be used. In addition, in a case in which the secret value generating unit 105 generates a secret-function value F(X) every time there is an inquiry from a user, the response data generating unit 107 may use the secret-function value F(X) generated at that time by the secret value generating unit 105.

From the viewpoint of further improvement of security, the one-way function may be appropriately updated. More specifically, the security data embedding device 10 may include an update unit, which is not illustrated, updating the one-way function. When the one-way function is updated by the update unit, the secret value generating unit 105 may generate a secret-function value F(X) by applying the corresponding one-way function to genome data and store the generated secret-function value F(X) in the secret value storing unit 106.

In such a case, the security data embedding device 10 may include an update data storing unit (not illustrated) storing data that is partial data of original data and is expected to be updated when the original data is initially registered. Then, the secret value generating unit 105 may generate (update)

a secret-function value F(X) by applying the updated one-way function to the corresponding partial data by referring to the update data storing unit.

In generation (updating) of the secret-function value F(X) using the secret value generating unit 105, referring to the update data storing unit is not necessary, and the genome data storing unit 104 may be referred to. More specifically, the secret value generating unit 105 may be configured to be able to access the genome data storing unit 104 only in a case in which the one-way function is updated by an updating unit. In such a case, the secret value generating unit 105 may extract data to be updated from the genome data storing unit 104 and generate a secret-function value F(X) by applying the updated one-way function to the extracted data.

In addition, from a viewpoint of expecting an increase in variations of contents of an inquiry in accordance with progress of genome analysis technologies and the like, the secret-function value F(X) stored in the secret value storing unit 106 may be also configured to be updatable. In such a case, for example, the device communication unit 101 receives update information from an external device. In the update information, information of a data position that is a target in the original data is included. In addition, in a case in which different one-way functions are applied to data positions, information of a one-way function corresponding to each data position may be included in the update information. For this reason, the secret value generating unit 105 may be accessible to the genome data storing unit 104 only in a case in which the device communication unit 101 receives update information. More specifically, the secret value generating unit 105 may extract new data from the genome data storing unit 104 on the basis of the update information and generate a new secret-function value F(X) by applying the one-way function to the extracted data.

In order for the secret value generating unit 105 to access the genome data storing unit 104, the secret value generating unit 105 and the genome data storing unit 104 may be connected, and the secret value generating unit 105 may be set to be accessible to the genome data storing unit 104 at the timing of updating.

FIG. 3 is a diagram illustrating an example of a user data table 70 stored in the secret value storing unit 106. The user data table 70 is a table in which extraction data, a data position, and a secret-function value F(X) are associated with each other for each user ID. A user ID is identification information that is used for identifying a user. Extraction data is a part or all of data that is focused on when genetic characteristics of a user are estimated.

A data position is a position of extraction data in original data in which bases are arranged (for example, a gene locus or a reference SNP ID number (RSID)). A secret-function value F(X) is a secret value acquired by applying a one-way function to extraction data. Although the extraction data and the secret-function value F(X) are different in accordance with a target for which genetic characteristics of a user are estimated (information representing an array of data positions and values of bases are different), for the convenience of description, the extraction data and the secret-function value are assumed to be similar to those illustrated in FIG. 3. In addition, in a case in which a secret-function value is generated by applying a different one-way function to extraction data of each data position, the one-way function applied to extraction data of each data position may also be stored in association with the extraction data, the data position, and the secret-function value F(X) in the user data table 70.

FIG. 4 is a diagram illustrating an example of an inquiry contents table 80 stored in the client device 20. As illustrated in FIG. 4, the inquiry contents table 80 is a data table in which an estimation target, comparison data, and a data position are associated with each other. The estimation target is a genetic characteristic of a user that is desired by the user. The comparison data is data that is used for judgment according to an estimation target. The data position represents a position (for example, a gene locus) of comparison data in original data in which bases are arranged. The client device 20 stores the inquiry contents table 80 in accordance with installation of a predetermined application therein.

Figure 5:
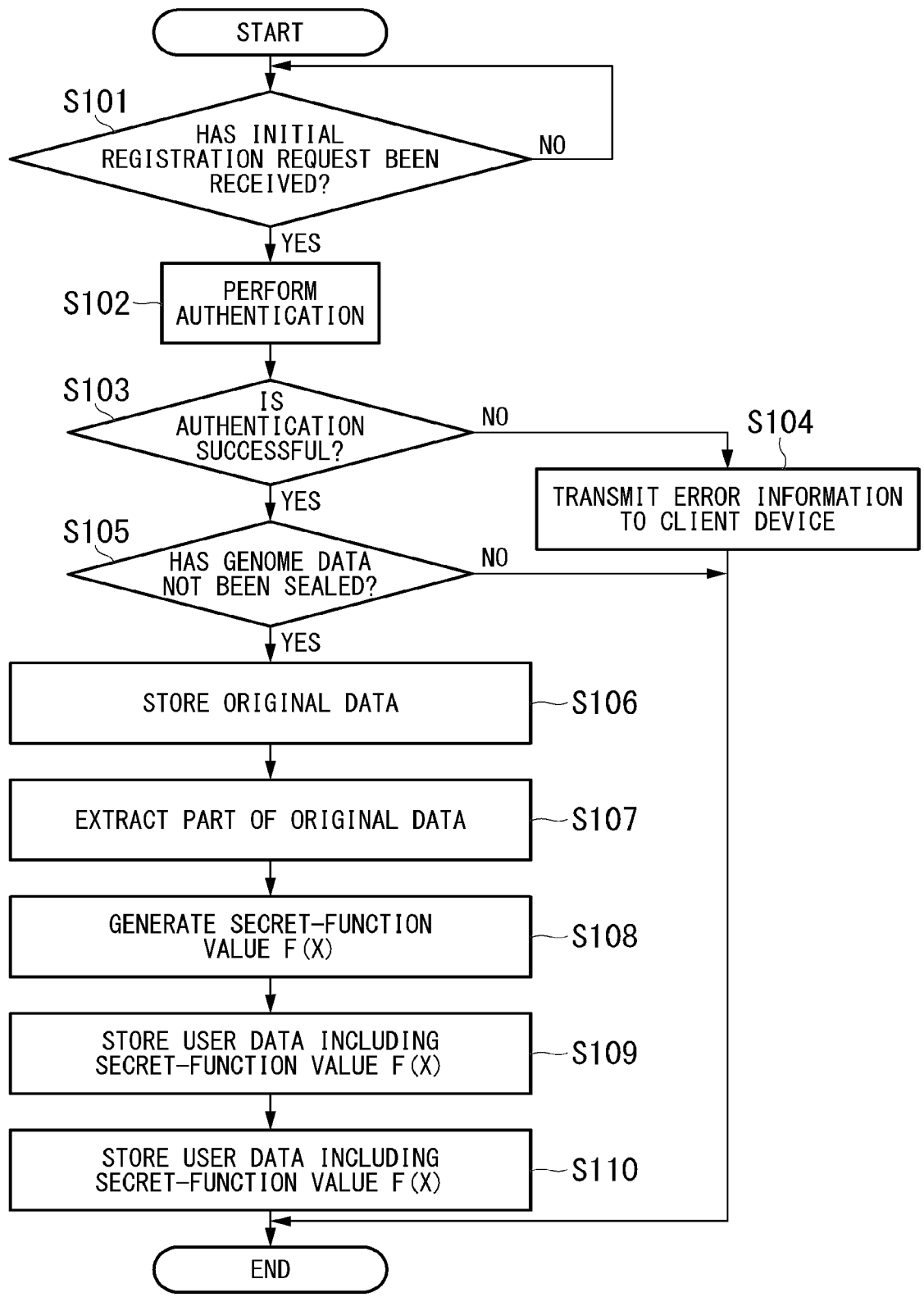
FIG. 5 is a flowchart illustrating an example of a process of registering genome data.

FIG. 5 is a flowchart illustrating an example of a process of registering genome data. In FIG. 5, the security data embedding device 10 judges whether or not a request for initial registration has been received by the device communication unit 101 from the client device 20 (Step S101). The security data embedding device 10 waits until the device communication unit 101 receives a request for initial registration (Step S101: No). When the device communication unit 101 receives a request for initial registration (Step S101: Yes), the authentication processing unit 102 performs authentication using authentication data included in the request for initial registration (Step S102).

In a case in which the authentication is unsuccessful (Step S103: No), the security data embedding device 10 transmits error information to the client device 20 from the device communication unit 101 (Step S104) and ends the process as it is. On the other hand, in a case in which the authentication is successful (Step S103: Yes), the data registering unit 103 judges whether or not genome data is sealed by referring to a sealing flag that indicates whether or not the genome data is stored in the genome data storing unit 104 (Step S105). In a case in which the genome data has been sealed in advance (Step S105: No), more specifically, in a case in which the sealing flag is "1 (on)", the security data embedding device 10 ends the process as it is.

On the other hand, in a case in which the genome data has not been embedded (Step S105: Yes), more specifically, in a case in which the embedding flag is "0 (off)", the data registering unit 103 causes the genome data storing unit 104 to store the original data (Step S106). Then, the data registering unit 103 extracts a part (or all) of the original data (Step S107). Next, the secret value generating unit 105 generates a secret-function value F(X) by applying a one-way function to a part (or all) of the original data (Step S108).

Then, the secret value generating unit 105 causes the secret value storing unit 106 to store user data including the secret-function value F(X) (Step S109). Then, the security data embedding device 10 transmits a result of the process to the client device 20 from the device communication unit 101 and ends the process (Step S110).

Next, a case in which genetic characteristics of a user are estimated on the basis of judgment of coincidence using a signal base sequence will be described.

Figure 6:
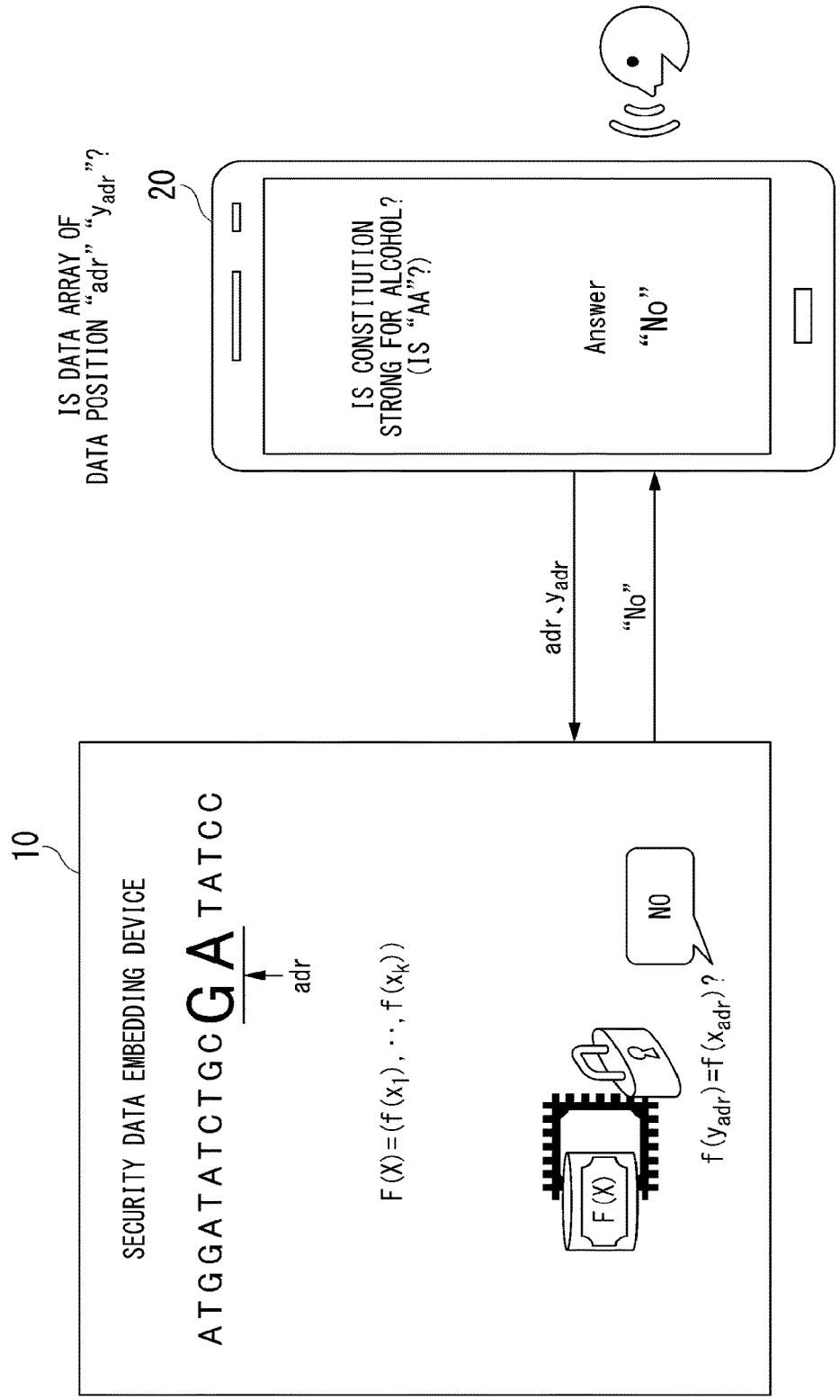
FIG. 6 is a diagram illustrating an example of generation of response data using a single base sequence.
Figure 7:
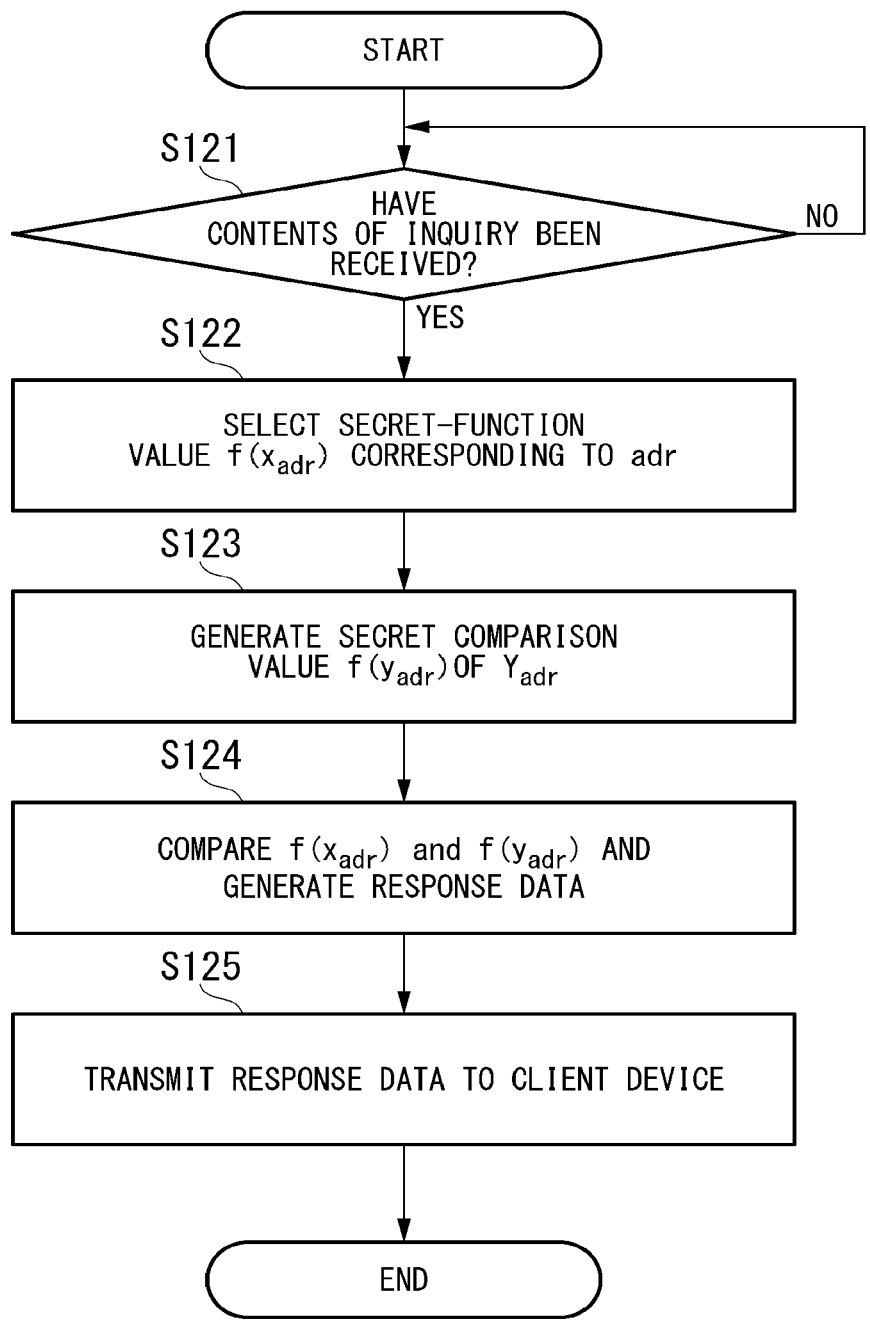
FIG. 7 is a flowchart illustrating an example of a process of generating response data using a single base sequence.

FIG. 6 is a diagram illustrating an example of generation of response data using a single base sequence. FIG. 7 is a flowchart illustrating an example of a process of generating response data using a single base sequence. In FIG. 6, it is assumed that a predetermined application has been operated in accordance with an operation of a user in the client device 20, and contents of an inquiry have been selected from the user. For example, it is assumed that contents of an inquiry about whether or not the user has a strong constitution for alcoholic drinks (alcohol tolerance) have been selected. In this case, the client device 20 transmits information (adr) of a data position representing a position of a base sequence used for estimating alcohol tolerance and comparison data $y_{adr}$ at the data position to the security data embedding device 10.

Then, as illustrated in FIG. 7, the security data embedding device 10 judges whether or not the device communication unit 101 has received contents of an inquiry from the client device 20 (Step S121). In the contents of the inquiry, the information of the data position (adr) and the comparison data $y_{adr}$ at the data position are included. The security data embedding device 10 waits until the device communication unit 101 receives the contents of the inquiry (Step S121: No).

When the device communication unit 101 has received the contents of the inquiry (Step S121: Yes), the response data generating unit 107 selects a secret-function value $f(x_{adr})$ corresponding to the designated data position (adr) among secret-function values F(X) by referring to the user data table 70 (FIG. 3) of the secret value storing unit 106 (Step S122). Then, the secret value generating unit 105 generates a secret comparison value $f(y_{adr})$ by applying a one-way function to the comparison data $y_{adr}$ included in the contents of the inquiry (Step S123).

Next, the response data generating unit 107 generates response data that indicates whether or not the secret-function value $f(x_{adr})$ and the secret comparison value $f(y_{adr})$ coincide with each other (Step S124). The, the security data embedding device 10 transmits the response data to the client device 20 from the device communication unit 101 and ends the process (Step S125). In accordance with this, as illustrated in FIG. 6, the client device 20 can present the response data to the inquiry to the user.

Next, a case in which a risk (riskiness) of diseases as genetic characteristics of a user is estimated on the basis of a genome-wide association analysis using single nucleotide polymorphism will be described. The single nucleotide polymorphism represents a phenomenon in which one base on a base sequence of genome is different between individuals. The genome-wide association analysis is an analysis method in which, mainly, a relation between frequencies of single nucleotide polymorphism (SNP) (a genotype and the like) and diseases and the like is statistically investigated using genotypes of the SNP.

Figure 8:
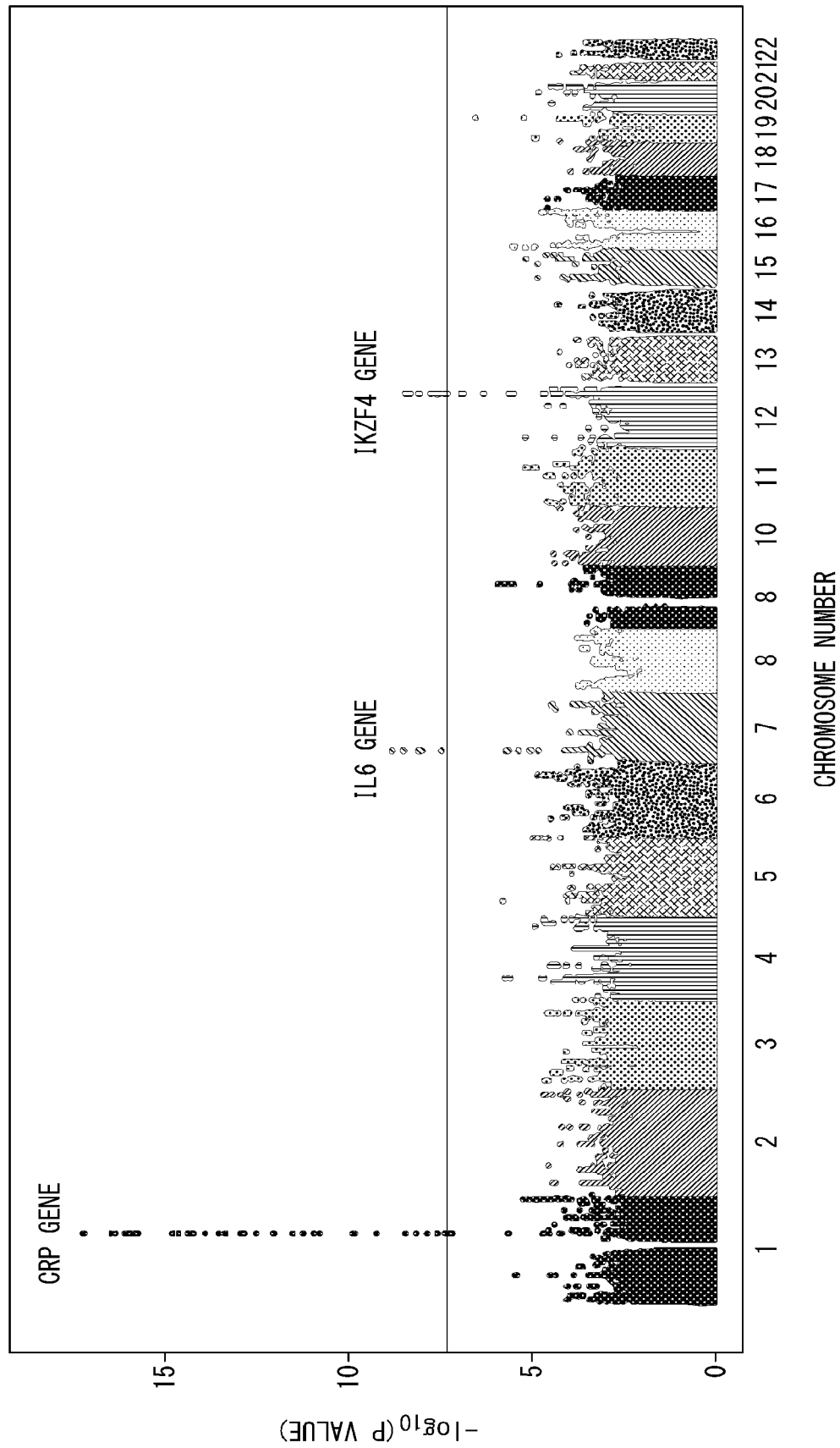
FIG. 8 is a diagram illustrating an example of an analysis result of a genome-wide association analysis using single nucleotide polymorphism.

FIG. 8 is a diagram illustrating an example of an analysis result of a genome-wide association analysis using single nucleotide polymorphism. In FIG. 8, the horizontal axis represents a position on a chromosome (chromosome number) at which single nucleotide polymorphism (SNP) is present. The vertical axis is a value that represents the strength of relevance of a disease (for example, asthma). All the genes illustrated in FIG. 8 such as a C-reactive protein (CRP) gene, an interleukin-6 (IL6) gene, and an IKAROS family zinc finger 4 (IKZF4) gene represent genes relating to asthma.

The CRP gene has a value correlated with the strength of an inflammatory reaction and is a gene that represents an index of inflammation. In addition, the IL6 gene is a gene that relates to an individual difference between values of CRP. The IKZF4 gene is a gene operating for differentiation of a specific cell.

Figure 9:
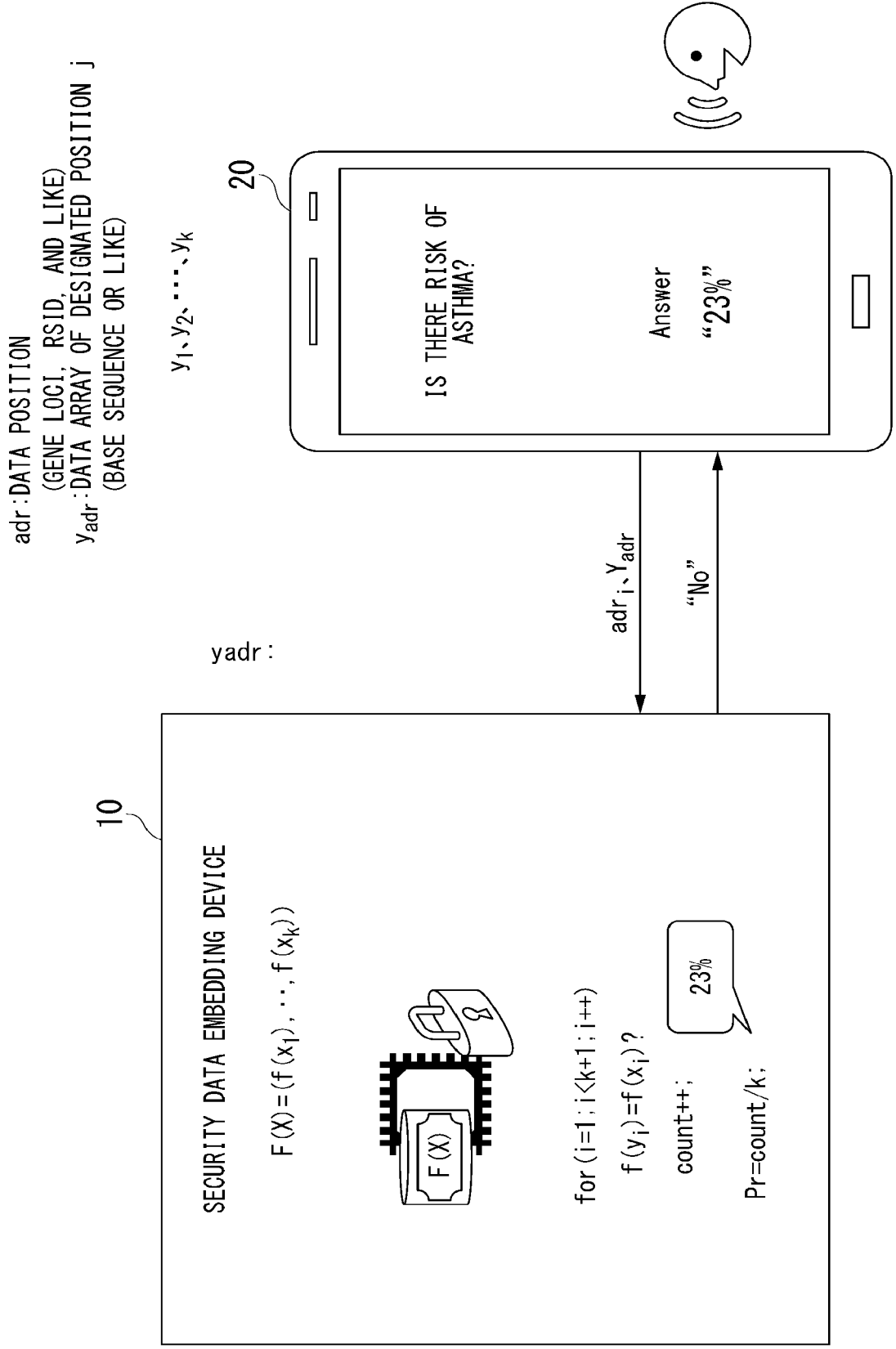
FIG. 9 is a diagram illustrating an example of generation of response data based on a genome-wide association analysis using single nucleotide polymorphism.
Figure 10:
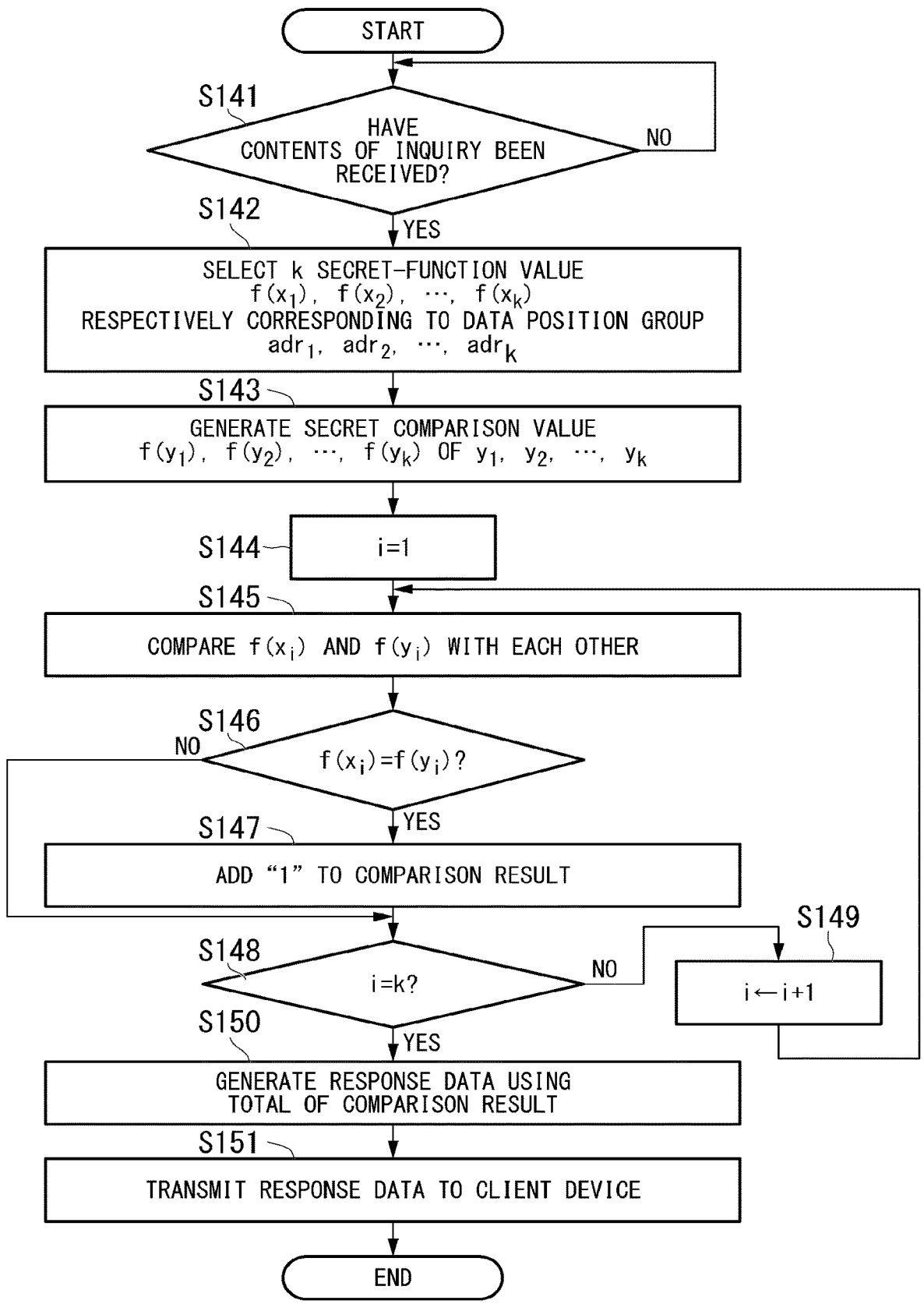
FIG. 10 is a flowchart illustrating an example of a process of generating response data based on a genome-wide association analysis using single nucleotide polymorphism.

FIG. 9 is a diagram illustrating an example of generation of response data based on a genome-wide association analysis using single nucleotide polymorphism. FIG. 10 is a flowchart illustrating an example of a process of generating response data based on a genome-wide association analysis using single nucleotide polymorphism. In FIG. 9, it is assumed that a predetermined application has been operated in accordance with an operation of a user in the client device 20, and contents of an inquiry have been selected from the user. For example, it is assumed that contents of an inquiry about the risk of a disease (for example, asthma) of the user have been selected. In this case, the client device 20 transmits information of data positions ($adr_i$ (here, i=1 to k)) representing positions in a base sequence (chromosome numbers) used for estimating the risk of asthma and k pieces of comparison data $y_i$ at the data positions to the security data embedding device 10.

Then, as illustrated in FIG. 10, the security data embedding device 10 judges whether or not the device communication unit 101 has received contents of an inquiry from the client device 20 (Step S141). In the contents of an inquiry, information ($adr_i$) of a plurality of (k) data positions (chromosome numbers) and k pieces of comparison data $y_i$ is included. The security data embedding device 10 waits until the device communication unit 101 receives contents of an inquiry (Step S141: No).

When the device communication unit 101 receives contents of an inquiry (Step S141: Yes), the response data generating unit 107 selects k secret-function values $f(x_i)$ respectively corresponding to a plurality of (k) designated data position groups ($adr_i$) among secret-function values F(X) by referring to the user data table 70 (see FIG. 3) of the secret value storing unit 106. Then, the secret value generating unit 105 generates secret comparison values $f(y_i)$ by applying a one-way function to each of the k pieces of comparison data $y_i$ included in the contents of the inquiry (Step S143).

Next, the response data generating unit 107 sets "1" to i (a value of one of 1 to k) corresponding to the number of pieces of data and data positions (Step S144). Then, the response data generating unit 107 compares the secret-function value $f(x_i)$ with the secret comparison value $f(y_i)$ (Step S145) and judges whether or not the secret-function value $f(x_i)$ and the secret comparison value $f(y_i)$ coincide with each other (Step S146). In a case in which the secret-function value $f(x_i)$ and the secret comparison value $f(y_i)$ do not coincide with each other (Step S146: No), the process proceeds to Step S148. In a case in which the secret-function value $f(x_i)$ and the secret comparison value $f(y_i)$ coincide with each other (Step S146. Yes), the response data generating unit 107 adds "1" to a comparison result (Step S147).

Then, the response data generating unit 107 judges whether or not i=k (Step S148). In a case in which "i=k" is not satisfied (Step S148: No), the response data generating unit 107 increments i (Step S149) and returns the process to Step S145. In a case in which i=k is satisfied (Step S148: Yes), the response data generating unit 107 generates response data using a total of comparison results (Step S150). The response data may be the number m of coincidences acquired by bit comparison of the secret-function value $f(x_i)$ with the secret comparison value $f(y_i)$ or may be a coincidence rate m/k acquired by dividing the number m of coincidences by the total number k.

Then, the security data embedding device 10 transmits the response data to the client device 20 from the device communication unit 101 and ends the process (Step S151). In accordance with this, as illustrated in FIG. 9, the client device 20 can present the response data to the inquiry to the user.

Next, a case in which a risk (riskiness) of a disease is estimated on the basis of a poly generic score as a genetic characteristic of a user will be described. The polygenic score is an analysis technique in which all the genomes are analyzed by weighting individual polymorphisms using analysis results of all the genomes on the premise that, in the case of a general disease, multiple gene loci having small effects (influences) relate to the disease.

Figure 11:
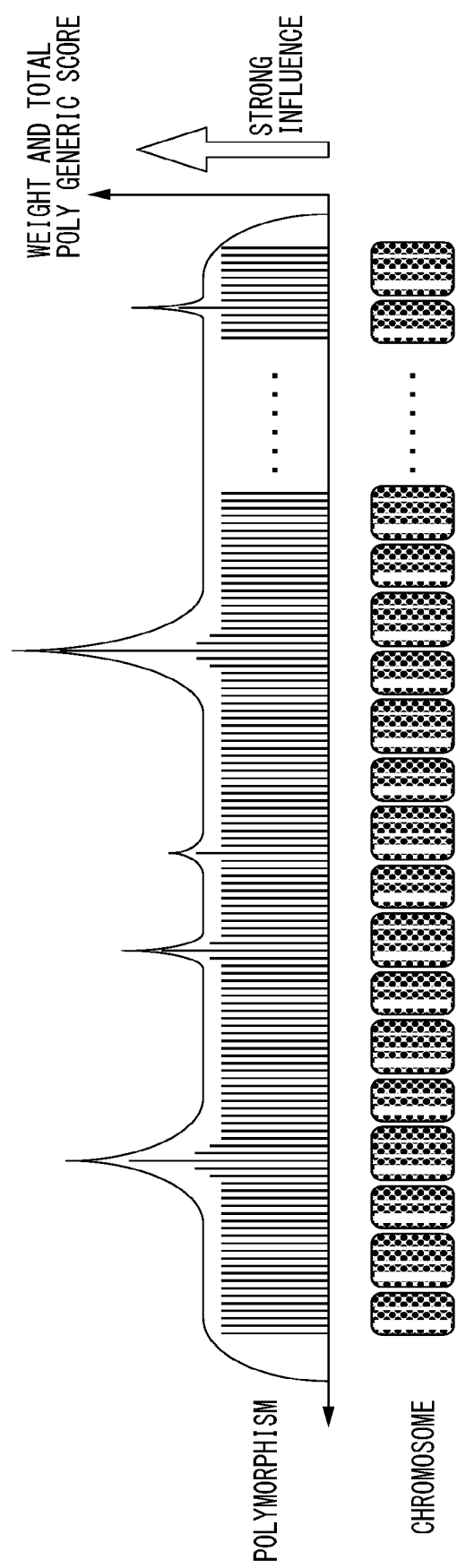
FIG. 11 is a diagram illustrating an example of a poly generic score.

FIG. 11 is a diagram illustrating an example of a poly generic score. In FIG. 11, similar to FIG. 8, the horizontal axis represents a position (a chromosome number) on a chromosome at which single nucleotide polymorphism (SNP) is present. The vertical axis, similar to FIG. 8, is a value representing the strength of relevance (influence) of a disease. As illustrated in FIG. 11, a polygenic score is a value acquired using all the genetic polymorphisms by weighting individual genetic polymorphisms and calculating a sum thereof.

Figure 12:
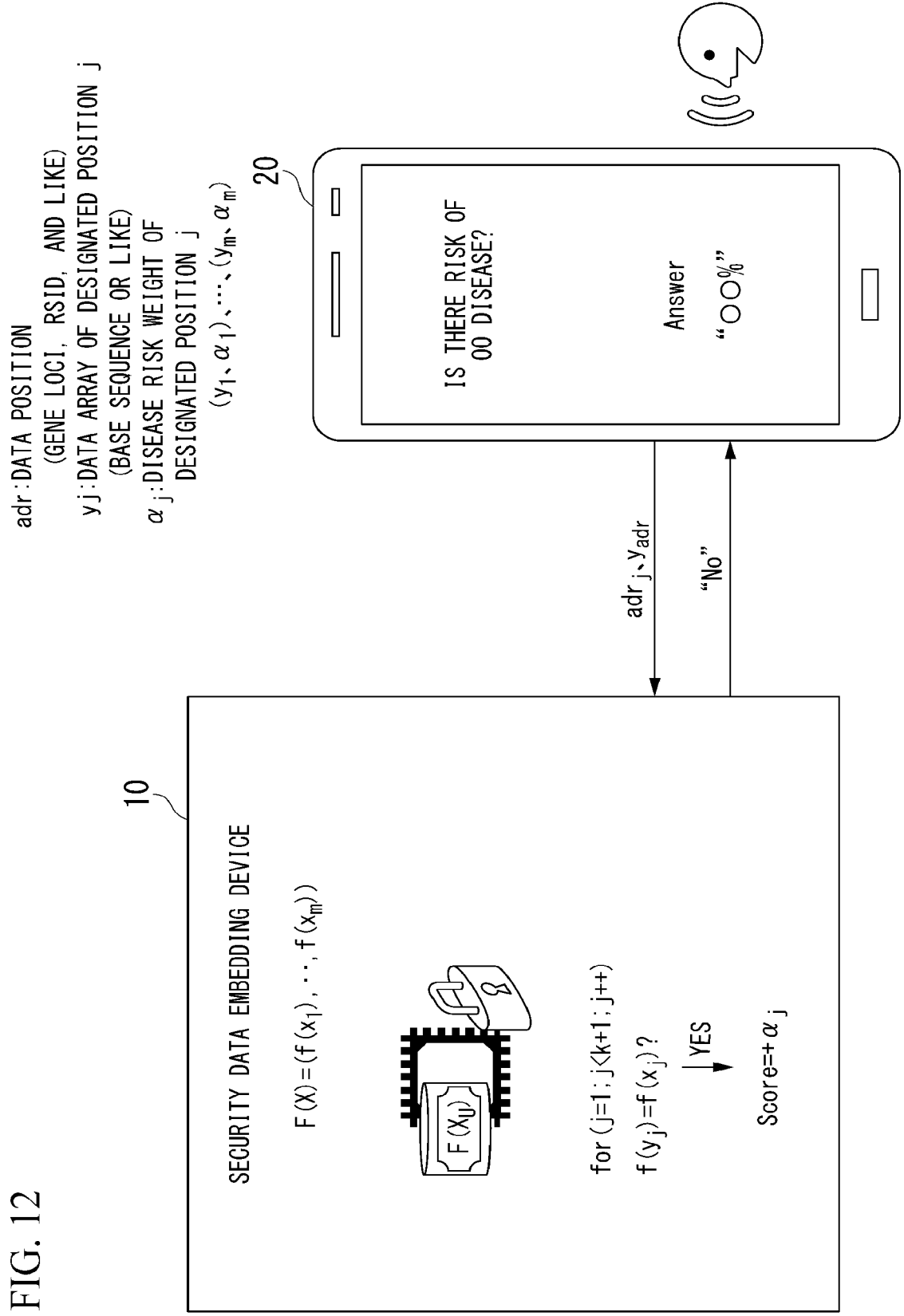
FIG. 12 is a diagram illustrating an example of generation of response data based on a polygenic score.
Figure 13:
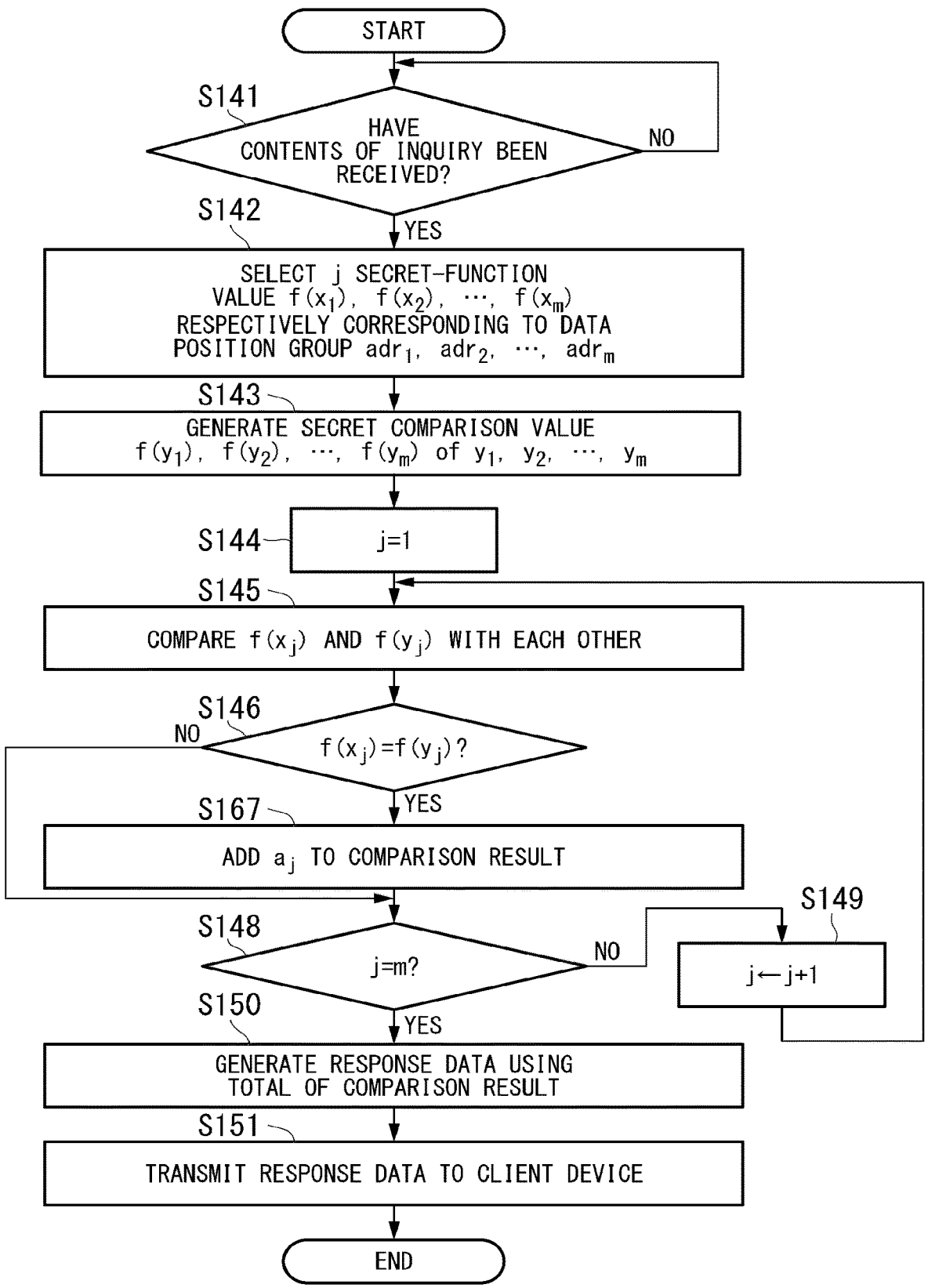
FIG. 13 is a flowchart illustrating an example of a process of generating response data based on a polygenic score.

FIG. 12 is a diagram illustrating an example of generation of response data based on a polygenic score. FIG. 13 is a flowchart illustrating an example of a process of generating response data based on a polygenic score. The process illustrated in FIG. 13 is different from the process illustrated in FIG. 10 in the process of Step S167 and in that the number of pieces of data to be compared is a total number (m) of pieces of data. In description of FIG. 13, points different from the process illustrated in FIG. 10 will be described.

In FIG. 12, it is assumed that a predetermined application has been operated in accordance with an operation of a user in the client device 20, and contents of an inquiry have been selected from the user. For example, it is assumed that contents of an inquiry about the risk of a disease (for example, anxiety) of the user have been selected. In this case, the client device 20 transmits information (adr) of data positions representing positions in a base sequence (chromosome numbers) used for estimating the risk about the inquiry and comparison data $y_{adr}$ at the data positions to the security data embedding device 10.

Step S141: As illustrated in FIG. 13, in the security data embedding device 10, the device communication unit 101 receives contents of an inquiry from the client device 20 (Step S141: Yes). In the contents of an inquiry, information ($adr_j$ (here, j=1 to m)) of a plurality of (m) data positions (chromosome numbers), m pieces of comparison data Yj at the data positions, and weights $α_j$ (here, j=1 to m) of the data positions are included. In the inquiry contents table 80 illustrated in FIG. 4, the weights $α_j$ are not illustrated.

Step S167: In a case in which the secret-function value $f(x_j)$ and the secret comparison value $f(y_j)$ coincide with each other (Step S146: Yes), the response data generating unit 107 adds "$α_j$" to a comparison result, and the process proceeds to Step S148.

In accordance with the process illustrated in FIG. 13, as illustrated in FIG. 12, the client device 20 can present response data for an inquiry to the user.

Next, in this embodiment, a form of an inquiry such as contents and the like of the inquiry are different for each user type, and this point will be described below.

FIG. 14 is a diagram illustrating an example of a form of an inquiry for each user type. In FIG. 14, a list 90 of forms of inquiries for each user type is a table in which a user type and a form of an inquiry are associated with each other. The user type represents either a medical worker or a general service. The medical worker, for example, is a doctor, a nurse, a pharmacist, a medical researcher, or the like. The general service, for example, is a general user other than a medical worker. Each user type also includes authentication of the user and is judged by the authentication processing unit 102, which is disposed in the security data embedding device 10, using authentication data from the client device 20 as an input. The judgment of a user type may be configured using a plurality of authentication technologies such as ID/password, biometric authentication, a common authentication code for each user type, and group authentication using a group signature indicating a member of a user type. Forms of an inquiry include Scene 1, Scene 2, Scene 3, the number of consecutive requests, and a command reception recovery time.

Scene 1 represents a form in which genetic characteristics of a user are estimated using a single base sequence. Scene 2 represents a form in which genetic characteristics of a user are estimated using an analysis result of a genome-wide association analysis using single nucleotide polymorphism. Scene 3 represents a form in which genetic characteristics of a user are estimated using a poly generic score value. The number of consecutive question requests is the number of inquiries that can be consecutively accepted. The command reception recovery time represents a time required until a next inquiry can be made after an inquiry is made.

In the case of a medical worker, an inquiry relating to any one of Scenes 1 to 3 can be made. In addition, in the case of a medical worker, the number of consecutive question requests is larger than that of the case of a general service, and the command reception recovery time is shorter than that of the case of a general service. On the other hand, in the case of a general service, although an inquiry relating to Scene 1 can be made, there is a restriction on an inquiry relating to Scene 2 that the chromosome number is up to three kinds, and an inquiry relating to Scene 3 cannot be made.

In this way, in comparison to a medical worker, each of items of other than Scene 1 is not permitted in a general service. The reason for this is that experts such as medical workers and the like need to multi dimensionally review detailed estimation results relating to genetic characteristics using genome data. In addition, if detailed estimation results are disclosed to a general user, an incorrect analysis may be made by the general user, and it may not be desirable ethically. A form in which medical workers are classified into doctors, nurses, pharmacists, and medical researchers, and each qualification and each type, and there are differences in handling/no-handling of each of the scenes described above and an upper limit of the number of consecutive question requests may be employed.

As described above, the security data embedding device 10 (a terminal device) according to the first embodiment generates response data on the basis of a secret-function value (a secret value) generated by applying a one-way function to genome data (original data) and contents of an inquiry and outputs the generated response data. Thus, response data can be generated without referring to the original data, and accordingly, the original data can be inhibited from leaking to the outside. In accordance with this, while the security is maintained strong, also to a general user other than medical workers, desired contents based on genome data of the user such as genetic characteristics of the user and the like can be presented.

In addition, the security data embedding device 10 according to the first embodiment includes the genome data storing unit 104 and generates a secret-function value by applying a one-way function to genome data at the time of being stored in the genome data storing unit 104. Thud, a secret-function value can be generated without accessing the genome data storing unit 104, and thus the security of the genome data can be configured to be strong.

In addition, the security data embedding device 10 according to the first embodiment generates a secret comparison value by applying a one-way function to comparison data included in an inquiry and generates response data on the basis of the secret-function value and the secret comparison value. Thus, response data can be generated only by acquiring comparison data without acquiring a secret comparison value from an external device, and accordingly, the convenience of the security data embedding device 10 can be improved.

In addition, the security data embedding device 10 according to the first embodiment includes the secret value storing unit 106, reads a secret-function value corresponding to an inquiry from among secret-function values stored in the secret value storing unit 106, and generates response data. Thus, in generation of response data, a secret-function value does not need to be generated at each time, and accordingly, a burden relating to the process at the time of generating response data can be reduced.

In addition, the security data embedding device 10 according to the first embodiment includes the genome data storing unit 104, and, when genome data (original data) is stored in the genome data storing unit 104, the corresponding genome data is prohibited from being output to the outside. Particularly, the genome data storing unit 104 is configured to be prohibited from outputting genome data to the outside using a hardware structure. For this reason, the security of genome data can be configured to be stronger.

In addition, the security data embedding device 10 according to the first embodiment generates response data using a secret-function value based on a single base sequence and a confidential comparison value. Thus, without referring to data of a single base sequence, genetic characteristics of a user can be presented.

In addition, the security data embedding device 10 according to the first embodiment generates response data using a secret-function value based on an analysis result of a genome-wide association analysis using single nucleotide polymorphism and a confidential comparison value. Accordingly, genetic characteristics of a user can be presented without referring to the value of the single nucleotide polymorphism.

In addition, the security data embedding device 10 according to the first embodiment generates response data using a secret-function value based on a poly generic score and a confidential comparison value. Accordingly, genetic characteristics of a user can be presented without referring to the value of the poly generic score.

In addition, the security data embedding device 10 according to the first embodiment may be configured to update a one-way function and update a secret-function value by applying the updated one-way function to genome data. In accordance with this, the one-way function can be inhibited from being broken by a third party, and the security of the original data can be configured to be stronger.

Modified Example 1 of First Embodiment

Next, Modified Example 1 of the first embodiment will be described. In Modified Example 1 of the first embodiment, a case in which no one-way function is configured to be stored will be described. In a case in which an input space for a one-way function is small, original data can be conjectured by performing brute force for the input space. In order to solve the relating problem, although the security data embedding device 10 according to the first embodiment stores the one-way function f, as described below, no one-way function may be configured to be stored.

Described more specifically, in initial registration, the device communication unit 101 receives a one-way function f in addition to original data of genome data and transmits the one-way function to the secret value generating unit 105 through the authentication processing unit 102 and the data registering unit 103. When a hiding process for all the extraction values X transmitted from the data registering unit 103 is completed, the secret value generating unit 105 eliminates the one-way function f.

For an inquiry about genome data, the device communication unit 101 receives a one-way function g in addition to contents Y of the inquiry and transmits them to the response data generating unit 107. The response data generating unit 107 generates response data on the basis of a secret value G(Y) calculated using the one-way function g.

In a case in which the one-way function f used at the time of initial registration and the one-way function g at the time of an inquiry are the same, correct response data is formed. For example, the one-way function f can be configured as f=(h, r) using a cryptographic hash function h such as SHA-2, SHA-3, or the like and a ransom number r. Here, $f(*)=h(r||*)$. Here, "||" represents bit connection.

In this way, by configuring such that the one-way function f is not stored in the security data embedding device, even when all the information stored in the secret value storing unit 106 and the secret value generating unit 105 leaks out, it becomes difficult to conjecture the original data of the genome data. More specifically, if data stored in the sealing device is read out, data required for matching is not provided, and thus it becomes difficult to identify original data.

In addition, only h in the one-way function f=(h, r) may be configured to be stored. In such a case, it is assumed that the device communication unit 101 receives r at the time of initial registration and at the time of making an inquiry about genome data.

In addition, at the time of initial registration, after receiving only h in addition to original data of genome data, the security data embedding device 10 may be configured to randomly generate r, output r to the outside at the time of completion of the initial registration, and then eliminate r. In the case of such a configuration, the security data embedding device 10 may include a random element generating unit that generates random element information.

Even when configured as such, in a case in which all the information stored in the secret value storing unit 106 and the secret value generating unit 105 leaks out, it can be caused to be difficult to conjecture original data of genome data.

Second Embodiment

Next, a second embodiment will be described. In the first embodiment described above, a configuration in which genetic characteristics of a user are estimated has been described. In the second embodiment, a configuration in which genetic characteristics of users are compared with each other will be described.

Figure 15:
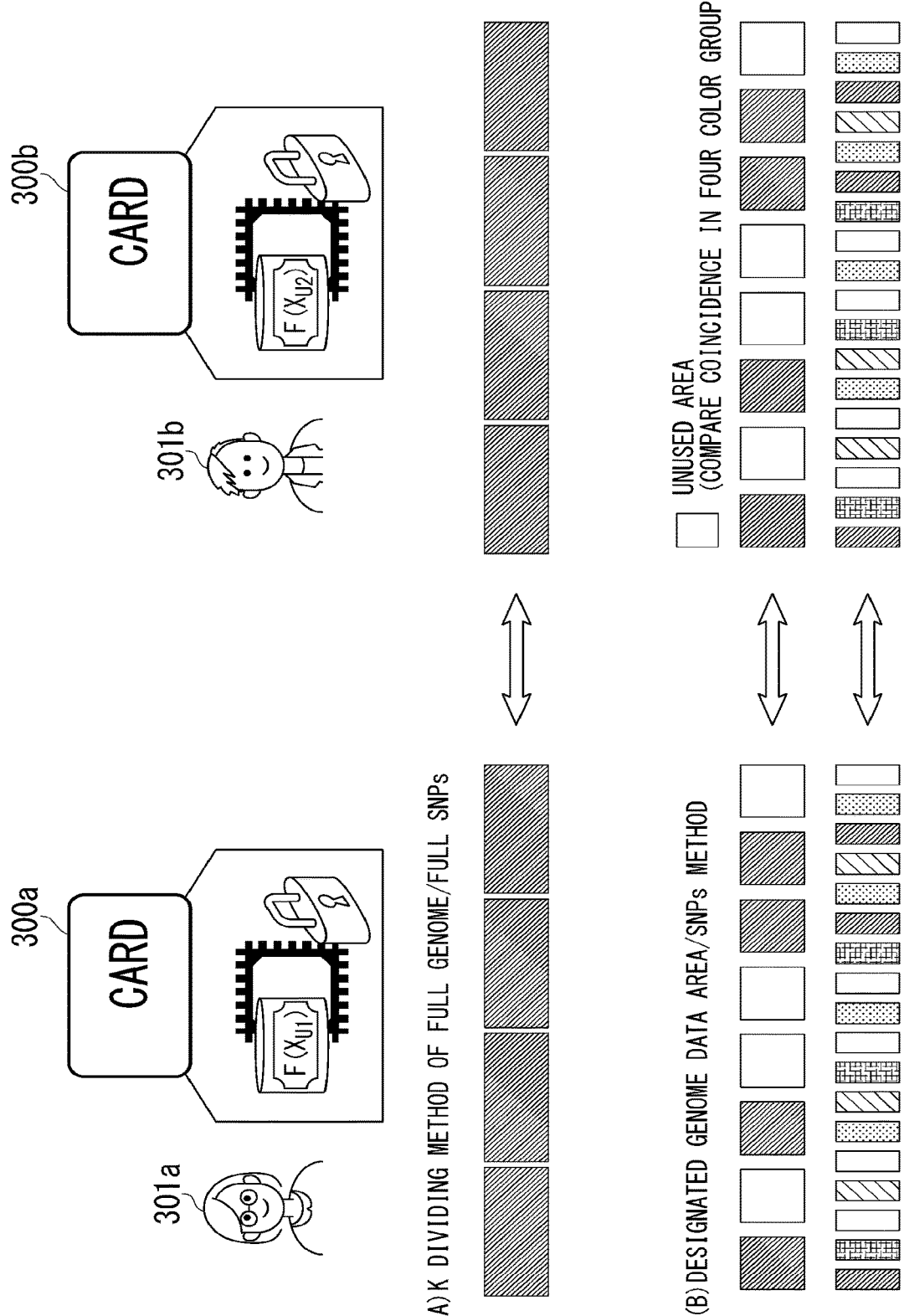
FIG. 15 is a diagram illustrating an example of a blocked base sequence.

FIG. 15 is a diagram illustrating an example of a blocked base sequence. As illustrated in FIG. 15, a user 301a owns an IC card 300a as a first storage device. A user 301b owns an IC card 300b as a second storage device. In the IC 300a, genome data (a secret-function value) of the user 301a to which a one-way function is applied is stored. Similarly, in the IC card 300b, genome data (a secret-function value) of the user 301b to which a one-way function is applied is stored. For example, the secret genome data is formed as blocks. For example, in (A) of FIG. 15, the entire secret genome data is divided into four blocks. For example, in a case in which the secret genome data is divided into n blocks, the secret genome data is stored as a secret-function value $F(X_{U[g]})$ (here, g=1 to n) for the user 301a, and the secret genome data is stored as a secret-function value $F(X_{Ug})$ for the user 301b. The secret-function values $F(X_{U[g]})$ (here, g=1 to n) formed as n blocks are composed of $f(x_{U[1]})$, $f(x_{U[2]})$, and $f(x_{U[n]})$. For example, as a configuration for comparing a degree of genetic similarity between users, a form in which, in units of a first block, a second block, a third block, and a fourth block (here, g=1, 2, 3, and 4), degrees of coincidence of output values using a hiding function are calculated, and degrees of coincidence in units of blocks are added up, whereby total coincidence rates such as 0%, 25%, 50%, 75% and higher are calculated may be employed.

In addition, the blocking pattern is not limited to division of the entire genome data into four parts. For example, as illustrated in an upper stage in (B) of FIG. 15, a pattern in which a designated area is divided into blocks may be used, or, as illustrated in a lower stage in (B), a pattern in which, by applying different hiding functions to four types of designated areas, the designated areas are formed as four types of blocks may be used. As a method for dividing into four types, a method in which designated areas are classified using a predetermined rule of grouping using relating gene loci and SNPs, for example, from information that is input or set in advance such as nationality, a relating disease, gender, and constitution may be used. In addition, the grouping rule may be changed each time in accordance with variation states at the time of performance such as weather information, a time, and a place. In addition, a form in which one of four types of blocks to which each gene locus or each SNP of genome data is assigned is determined each time using random element information generated by the random element generating unit 108 (see FIG. 18) as an input may be employed. Furthermore, in FIG. 15, although the IC cards 300 are illustrated as examples of storage devices (the first storage device and the second storage device) storing secret-function values, the storage devices are not limited to the IC cards 300 and may be smartphones, portable phones, or the like.

Figure 16:
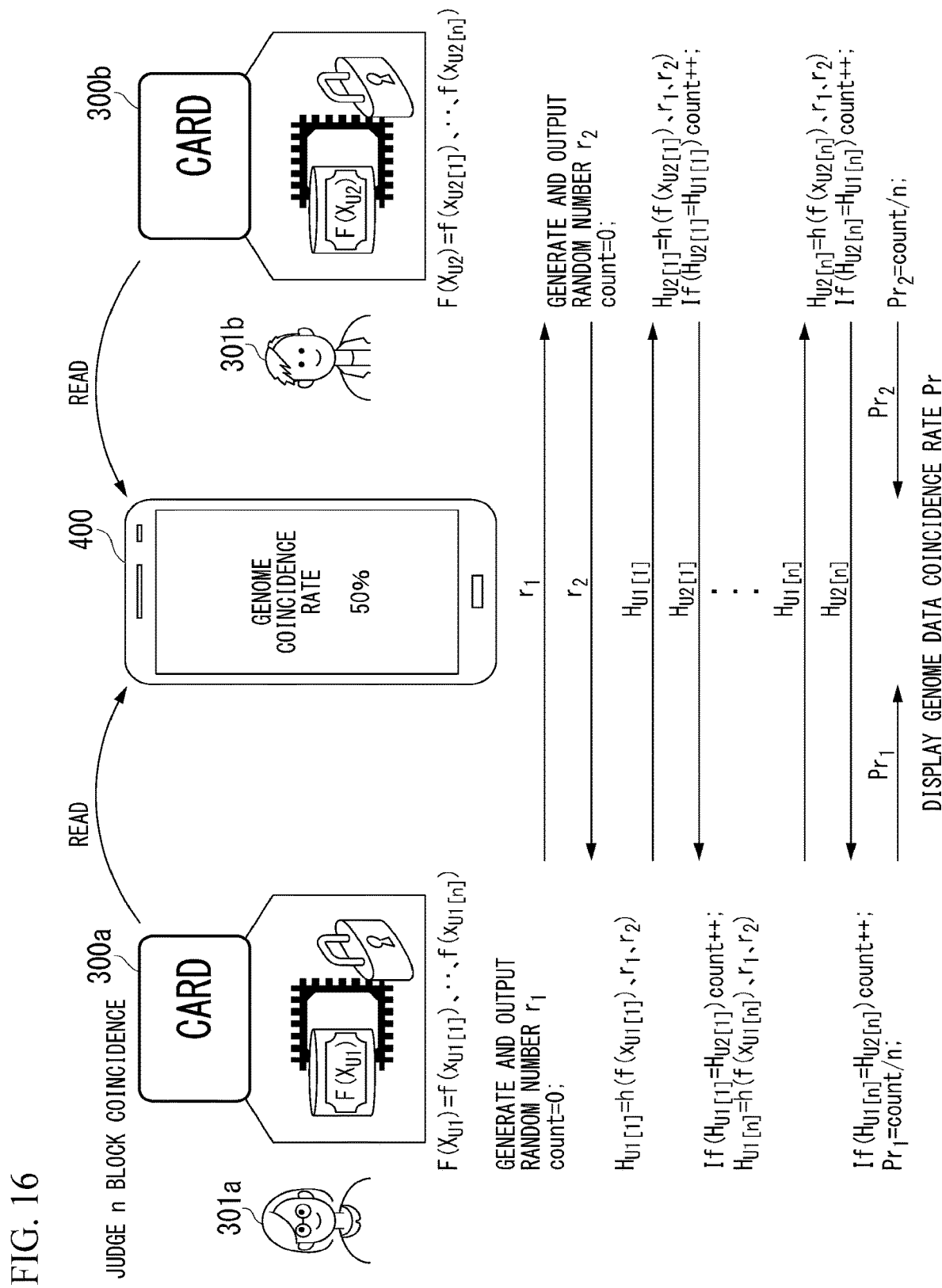
FIG. 16 is a diagram illustrating an example of generation of response data based on comparison results between genetic characteristics of users.
Figure 17:
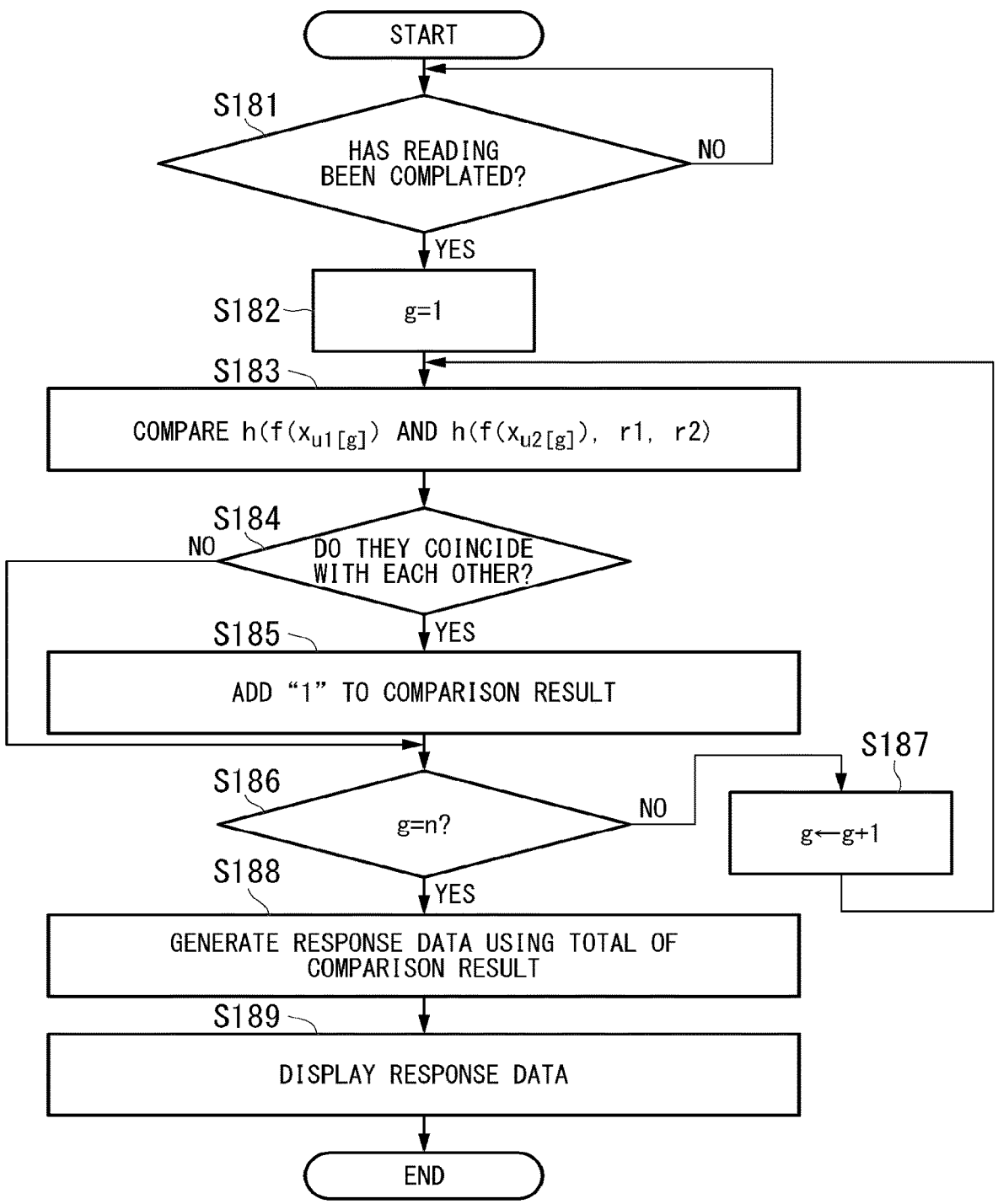
FIG. 17 is a flowchart illustrating an example of a process of generating response data based on comparison results between genetic characteristics of users.

FIG. 16 is a diagram illustrating an example of generation of response data based on comparison results between genetic characteristics of users. FIG. 17 is a flowchart illustrating an example of a process of generating response data on the basis of comparison results between genetic characteristics of users.

Figure 18:
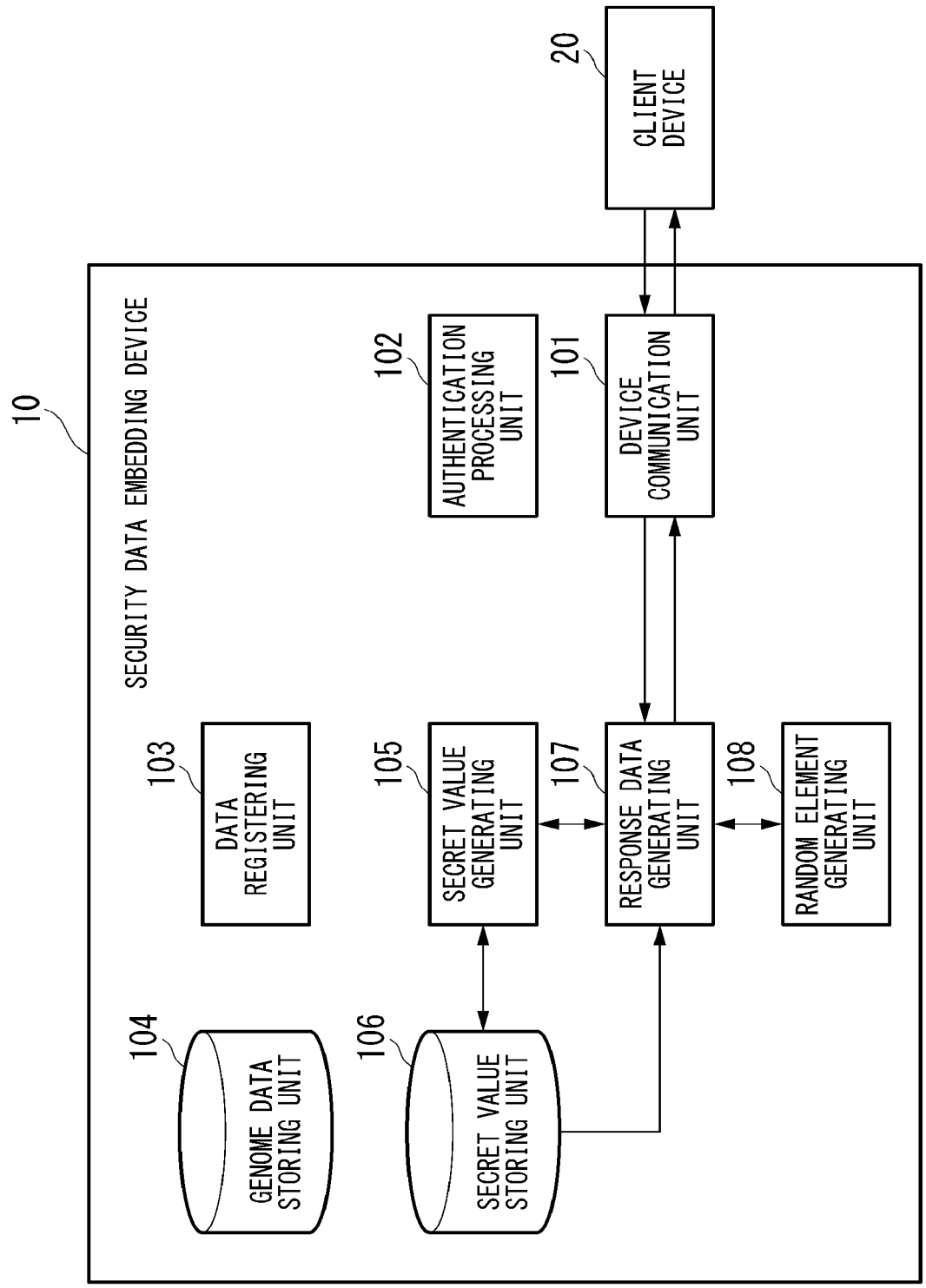
FIG. 18 is a schematic block diagram illustrating the configuration of functional blocks of a sealing system 2 according to this embodiment.

FIG. 18 is a schematic block diagram illustrating the configuration of functional blocks of a sealing system 2 according to this embodiment. The security data embedding device 10 includes a device communication unit 101, an authentication processing unit 102, a data registering unit 103, a genome data storing unit 104, a secret value generating unit 105, a secret value storing unit 106, a response data generating unit 107, and a random element generating unit 108.

In FIG. 16, a display device 400 is an example of a terminal device. For example, the display device 400 is a smartphone, a tablet device, or a terminal device, which is installed in a store, including a display device. The display device 400 has a function of reading calculation processing result values from the IC cards 300a and 300b (the function of the device communication unit 101) and a function of transmitting the read calculation processing values to one of the IC cards 300a and 300b. In addition, the display device 400 has a display unit that compares calculated values of the cards that are calculated by composing secret-function values of mutual genome data stored in the IC cards 300a and 300b and a common random element value and displays a value acquired by calculating a degree of coincidence thereof. In the display device 400, a predetermined application used for realizing such functions is installed. In addition, the display device 400 may be a dedicated computer device having such functions. In FIG. 16, although a form in which comparison of calculated values of the cards that are calculated by composing secret-function values of mutual genome data and a common random element value and calculation of a degree of coincidence thereof are processed inside the cards is illustrated, a form in which comparison of the calculated values of the cards and calculation of the degree of coincidence thereof is executed by the display device 400 may be employed. Hereinafter, the flow of a process in a form in which comparison of calculated values of cards and calculation of a degree of coincidence thereof are executed by the display device 400 will be described.

It is assumed that a predetermined application has been operated in the display device 400 in accordance with an operation of a user 301, and an indication for performing judgment of a degree of coincidence between users 301a and 301b has been selected from the user 301. Then, the display device 400 performs notification of an indication for causing a predetermined reading unit included in the display device 400 to read the IC cards 300a and 300b on a display screen.

Then, as illustrated in FIG. 17, the display device 400 judges whether or not reading has been completed using the function of the device communication unit 101 (Step S181). When reading has been completed, the response data generating unit 107 sets "1" to g (a value of one of 1 to n) representing the number of blocks of genome data (Step S182). Then, the response data generating unit 107 compares a function value $H(F(X_{U1}), r1, r2)$ based on the secret-function value $F(X_{U1})$ of the user 301a and a function value $H(F(X_{U2}), r1, r2)$ based on the secret-function value $F(X_{U2})$ of the user 301b with each other. In addition, r1 is a random element value generated by the random element generating unit 108 of the IC card 300a. r2 is a random element value generated by the random element generating unit 108 of the IC card 300b. Then, the response data generating unit 107 compares a function value $h(f(x_{U1}[g]), r1, r2) = H_{U1}[g]$ based on the secret-function value $f(x_{U1}[g])$ (here, g=1 to n) and a function value $h(f(x_{U2}[g]), r1, r2) = H_{U2}[g]$ based on the secret-function value $f(x_{U2}[g])$ with each other (Step S183).

Next, the response data generating unit 107 judges whether or not the function value $h(f(x_{U1}[g]), r1, r2)$ and the function value $h(f(x_{U2}[g]), r1, r2)$ coincide with each other (Step S184). In a case in which the function value $h(f(x_{U1}[g]), r1, r2)$ and the function value $h(f(x_{U2}[g]), r1, r2)$ do not coincide with each other (Step S184: No), the process proceeds to Step S186. In a case in which the function value $h(f(x_{U1}[g]), r1, r2)$ and the function value $h(f(x_{U2}[g]), r1, r2)$ coincide with each other (Step S184. Yes), the response data generating unit 107 adds "1" to the comparison result (Step S185).

Then, the response data generating unit 107 judges whether or not g=n is satisfied (Step S186). In a case in which "g=n" is not satisfied (Step S186: No), the response data generating unit 107 increments g (Step S187), and the process is returned to Step S183. In a case in which g=n is satisfied (Step S186: Yes), the response data generating unit 107 generates response data using the comparison result (Step S188). The response data, for example, is a coincidence rate that is acquired by dividing the number of coincidences (the comparison result) by a total number n.

Then, the display unit of the display device 400 displays the response data and ends a series of processes (Step S189). In this way, as illustrated in FIG. 16, the coincidence rate of the users 301a and 301b can be displayed. In addition, when secret genome data is divided into four blocks, and secret-function values of the blocks coincide with each other, the coincidence rate is 100%. However, the coincidence rate of the genome data cannot be 100% between the users 301a and 301b. For this reason, in a case in which the coincidence rate is 100%, the response data generating unit 107 may change the coincidence rate to a coincidence rate representing less than 100% such as "75% or higher" and generate response data.

As described above, the display device 400 (a terminal device) according to the second embodiment compares secret values of the IC cards 300a and 300b in which secret-function values are stored and generates and outputs response data based on a result of the comparison. Thus, response data can be generated without referring to the original data, and accordingly, the original data can be inhibited from leaking to the outside. For this reason, while the security of the original data is maintained strong, contents of an inquiry desired by a user such as a coincidence rate of genetic characteristics between users or the like can be presented. In addition, a match or the like between both users can be conjectured by the users 301a and 301b from the genome data of the users 301a and 301b, and accordingly, the presented contents of an inquiry (the coincidence rate) can help for selecting a person or be applied to a play. Therefore, according to the second embodiment, a novel display device 400 (a terminal device) can be provided.

In addition, at least some of the functions of the sealing system 1 according to the embodiment described above may be configured to be realized by a computer. In such a case, a program used for realizing such functions may be recorded on a computer-readable recording medium. In addition, the functions may be realized by causing a computer system to read and execute the program recorded on this recording medium. The "computer system" described here includes an operating system (OS) and hardware such as peripherals. Furthermore, the "computer-readable recording medium" represents a storage device such as a hard disk or the like built into the computer system. The storage device also includes portable media such as a flexible disk, a magneto-optical disk, a ROM, a CD-ROM, a DVD-ROM, a USB memory, and the like. Furthermore, the "computer-readable recording medium" may be a medium that dynamically maintains a program during a short time. More specifically, the medium is a communication line in a case in which a program is transmitted through a communication line such as a network including the Internet or the like, a telephone line, or the like. In addition, the "computer-readable recording medium" may include a medium that maintains a program for a predetermined time. More specifically, the medium is an internal volatile memory or the like of a computer system serving as a server or a client. In addition, the program described above may be used for realizing a part of the functions described above. Furthermore, the program described may be a program that can realize the functions described above in combination with a program that has already been recorded in a computer system.

While certain embodiments of the present invention have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

The invention claimed is:

1. A terminal device comprising:
   a memory that stores a set of software program;
   a hardware processor configured to execute the set of software program in the memory, to cause the hardware processor, when the set of software program is executed, to perform a set of operations which comprise:
   accepting an inquiry about genome data of each user; wherein the inquiry includes comparison data relative to one or more values of one or more basis at a position of a base sequence of the genome data;
   generating a secret value by applying a one-way function to the one or more values of the one or more basis at the position of the genome data, wherein the one or more values are data that are extracted from at least a part of the genome data;
   generating a secret comparison value by applying the one-way function to the comparison data;
   generating response data by comparing the secret value and the secret comparison value, wherein the response data indicates whether or not the secret value and the secret comparison value coincide with each other; and
   outputting the response data generated.

2. The terminal device according to claim 1, further comprising a genome data memory that stores the genome data,
   wherein generating the secret value comprises generating the secret value by applying the one-way function to the data that are extracted from the at least part of the genome data stored in the genome data memory.

3. The terminal device according to claim 1, further comprising a secret value memory that stores a secret-function value,
   wherein the response data indicates a result of comparison between the secret-function value stored in the secret value memory and the secret comparison value generated.

4. The terminal device according to claim 1, further comprising a genome data memory that stores the genome data,
   wherein the genome data memory is configured to prohibit the genome data from being output from the genome data memory after the genome data is once stored in the genome data memory.

5. The terminal device according to claim 4, further comprising a data registering processor that is wired to be exclusively connectable with the genome data memory for allowing only the data registering unit to write the genome data into the genome data memory.

6. A terminal device comprising:
   a memory that stores a set of software program:
   a hardware processor configured to execute the set of software program stored in the memory, to cause the hardware processor, when the set of software program is executed, to perform a set of operations which comprise;
   accepting an inquiry about genome data of each user, wherein the inquiry includes comparison data relative to one or more values of one or more specific basis of the genome data;

generating a secret value by applying a one-way function to the one or more values of the one or more specific basis of the genome data, wherein the one or more values are data that are extracted from at least a part of the genome data;

generating a secret comparison value by applying the one-way function to the comparison data;

generating response data by comparing the secret value and the secret comparison value, wherein the response data indicates whether or not the secret value and the secret comparison value coincide with each other; and outputting the response data generated.

7. A terminal device comprising:

a memory that stores a set of software program;

a hardware processor configured to execute the set of software program stored in the memory, to cause the hardware processor, when the set of software program is executed, to perform a set of operations which comprise:

accepting and inquiry about genome data of each user, wherein the inquiry includes comparison data relative to all values of all basis of the genome data;

generating a secret value by applying a one-way function to all values of the all basis of the genome data, wherein the all values are data that are extracted from all of the genome data;

generating a secret comparison value by applying the one-way function to the comparison data;

generating response data by comparing the secret value and the secret comparison value, wherein the response data indicates whether or not the secret value and the secret comparison value coincide with each other; and outputting the response data generated.

8. A data processing method using a computer, the data processing method comprising:

accepting an inquiry about genome data of each user, wherein the inquiry includes comparison data relative to one or more values of one or more basis at a position of a base sequence of the genome data;

generating a secret value by applying a one-way function to the one or more values of the one or more basis at the position of the genome data, wherein the one or more values ara data that are extracted from at least a part of the genome data;

generating a secret comparison value by applying the one-way function to the comparison data;

generating response data by comparing the secret value and the secret comparison value, wherein the response indicates whether or not the secret value and the secret comparison value coincide with each other; and outputting the response data generated.

9. A non-transitory storage medium that stores hardware-processor-executable program that, when executed by a hardware-processor to execute, causes the hardware-processor to perform a set of operations which comprises:

accepting an inquiry about genome data of each data user, wherein the inquiry includes comparison data relative to one or more values of one or more basis at a position of a base sequence of the genome data:

generating a secret value by applying a one-way function to the one or more values of the one or more basis at the position of the genome data, wherein the one or more values are data that are extracted from at least a part of the genome data;

generating a secret comparison value by applying the one-way function to the comparison data;

generating response data by comparing the secret value and the secret comparison value, wherein the response data indicates whether or not the secret value and the secret comparison value coincide with each other; and outputting the response data generated.

* * * * *